United States Patent
Nishio et al.

(10) Patent No.: US 11,517,590 B2
(45) Date of Patent: Dec. 6, 2022

(54) METHOD FOR PREPARING GENETICALLY-MODIFIED T CELLS WHICH EXPRESS CHIMERIC ANTIGEN RECEPTOR

(71) Applicant: NATIONAL UNIVERSITY CORPORATION TOKAI NATIONAL HIGHER EDUCATION AND RESEARCH SYSTEM, Nagoya (JP)

(72) Inventors: Nobuhiro Nishio, Nagoya (JP); Yozo Nakazawa, Matsumoto (JP); Miyuki Tanaka, Matsumoto (JP); Daisuke Morita, Matsumoto (JP); Yoshiyuki Takahashi, Nagoya (JP)

(73) Assignee: NATIONAL UNIVERSITY CORPORATION TOKAI NATIONAL HIGHER EDUCATION AND RESEARCH SYSTEM, Nagoya (JP)

(*) Notice: Subject to any disclaimer, the term of this patent is extended or adjusted under 35 U.S.C. 154(b) by 348 days.

(21) Appl. No.: 15/766,380

(22) PCT Filed: Oct. 7, 2016

(86) PCT No.: PCT/JP2016/079989
§ 371 (c)(1),
(2) Date: Apr. 6, 2018

(87) PCT Pub. No.: WO2017/061615
PCT Pub. Date: Apr. 13, 2017

(65) Prior Publication Data
US 2018/0289742 A1    Oct. 11, 2018

(30) Foreign Application Priority Data
Oct. 8, 2015   (JP) .............................. JP2015-200458

(51) Int. Cl.
| | | |
|---|---|---|
| *A61K 35/17* | (2015.01) |
| *C12N 5/10* | (2006.01) |
| *A61P 35/00* | (2006.01) |
| *C07K 14/725* | (2006.01) |
| *C12N 5/0783* | (2010.01) |
| *A61K 39/00* | (2006.01) |
| *C07K 19/00* | (2006.01) |
| *C07K 14/705* | (2006.01) |
| *C12N 15/09* | (2006.01) |
| *C07K 14/075* | (2006.01) |
| *C12N 5/16* | (2006.01) |

(52) U.S. Cl.
CPC .............. *A61K 35/17* (2013.01); *A61P 35/00* (2018.01); *C07K 14/075* (2013.01); *C07K 14/705* (2013.01); *C07K 14/7051* (2013.01); *C07K 14/70521* (2013.01); *C07K 19/00* (2013.01); *C12N 5/0636* (2013.01); *C12N 5/0646* (2013.01); *C12N 5/10* (2013.01); *C12N 5/163* (2013.01); *C12N 15/09* (2013.01); *A61K 2039/5156* (2013.01); *A61K 2039/5158* (2013.01); *A61K 2039/585* (2013.01)

(58) Field of Classification Search
CPC .... A61K 2039/5156; A61K 2039/5158; A61K 2039/585
See application file for complete search history.

(56) References Cited

U.S. PATENT DOCUMENTS

| | | | | |
|---|---|---|---|---|
| 2007/0036773 A1* | 2/2007 | Cooper | .................. | A61K 48/00 424/93.21 |
| 2013/0287748 A1* | 10/2013 | June | ........................ | A61P 37/02 424/93.21 |
| 2015/0017723 A1* | 1/2015 | Rooney | ................ | C12N 5/0638 435/377 |

FOREIGN PATENT DOCUMENTS

WO   2013/088114 A1   6/2013

OTHER PUBLICATIONS

Saito et al. Cytotherapy, 2014; 16: 1257-1269 (Year: 2014).*
Nakazawa et al. J Immunother. Oct. 2009; 32(8): 826-836. (Year: 2009).*
Manuri et al. Human Gene Therapy 21:427-437 (Apr. 2010) (Year: 2010).*
Nakazawa et al.PiggyBac-mediated Cancer Immunotherapy Using EBV-specific Cytotoxic T-cells Expressing HER2 specific Chimeric Antigen Receptor.Molecular Therapy vol. 19 No. 12, 2133-2143 Dec. 2011. (Year: 2011).*

(Continued)

*Primary Examiner* — Daniel E Kolker
*Assistant Examiner* — Brian Hartnett
(74) *Attorney, Agent, or Firm* — Locke Lord LLP

(57) ABSTRACT

In order to improve the efficiency of gene introduction in CAR therapy employing a transposon method, provided is a method for preparing genetically-modified T cells expressing chimeric antigen receptor, comprising: (1) a step of preparing non-proliferative cells which are obtained by stimulating a group of cells comprising T cells using an anti-CD3 antibody and an anti-CD28 antibody followed by a treatment for causing the cells to lose their proliferation capability; (2) a step of obtaining genetically-modified T cells into which a target antigen-specific chimeric antigen receptor gene has been introduced using a transposon method; (3) a step of mixing the non-proliferative cells prepared by step (1) with the genetically-modified T cells obtained by step (2), and co-culturing the mixed cells while stimulating the mixed cells using an anti-CD3 antibody and anti-CD28 antibody; and (4) a step of collecting the cells after culture.

11 Claims, 13 Drawing Sheets
Specification includes a Sequence Listing.

(56) References Cited

OTHER PUBLICATIONS

Singh Harjeet et al., "Manufacture of Clinical-Grade CD 19-Specific T Cells Stably Expressing Chimeric Antigen Receptor Using Sleeping Beauty System and Artificial Antigen Presenting Cells", PLOS ONE, vol. 8, No. 5, 2013, pp. 1-11. (cited in the Mar. 15, 2019 Search Report issued for EP16853766.0).

Daisuke Morita et al., "Enhancement of CAR Expression of piggyBac Transposon-Engineered T Cells by Stimulation with Viral Antigens" Molecular Therapy Volume Copyright The American Society of Gene & Cell Therapy, vol. 24, No. 1, May 1, 2016, pp. S278-S279. (cited in the Mar. 15, 2019 Search Report issued for EP16853766.0).

Daisuke Morita et al., "Enhanced Expression of Anti-CD19 Chimeric Antigen Receptor in piggyBac Transposon-Engineered T Cells", Molecular Therap—Methods & Clinical Develop, vol. 8, Mar. 1, 2018, pp. 131-140. (cited in the Mar. 15, 2019 Search Report issued for EP16853766.0).

Supplementary European Search Report dated Mar. 15, 2019, issued for the European patent application No. 16853766.0.

S. A. Grupp et al., "Chimeric Antigen Receptor-Modified T Cells for Acute Lymphoid Leukemia," The New England Journal Medicine (2013) 368: pp. 1509-1518 (discussed in the spec).

S. L. Maude et al., "Chimeric Antigen Receptor T Cells for Sustained Remissions in Leukemia," The New England Journal Medicine (2014) 371: pp. 1507-1517 (discussed in the spec).

D. W. Lee et al., "T cells expressing CD19 Chimeric actigen receptors for acute lymphoblastic leukaemia in children and young adults: a phase 1 dose-escalation trial," The Lancet (2014) 385(9967): pp. 1-12 and Supplementary appendix (discussed in the spec).

R. A. Morgan et al., "Faster, Cheaper, Safer, T cell engineering," J Immunother (2013) 36(1): pp. 1-3. (discussed in the spec).

S. Saito et al., "Anti-leukemic potency of piggyBac-mediated CD19-specific T cells against refractory Philadelphia chromosome-positive acute lymphoblastic leukemia," Cytotherapy, vol. 16, No. 9, 2014, pp. 1257-1269, (cited in the ISR).

Yozo Nakazawa, "Gene-modified T-cell Therapy Using Chimeric Antigen Receptor," The Shinshu Medical Journal, vol. 61, No. 4, 2013, pp. 197-203. (cited in the ISR; Relevancy of this reference is stated in the Written Opinion of the International searching authority).

D. C. Deniger et al., "Sleeping Beauty Transposition of Chimeric Antigen Receptors Targeting Receptor Tyrosine Kinase-Like Orphan Receptor-1 (ROR1) into Diverse Memory T-cell Populations," PLOS ONE, Jun. 1, 2015, 10(6): e0128151, pp. 1-19. (cited in the ISR).

D. L. Galvan et al., "Genome-Wide Mapping of PiggyBac Transposon Integrations in Primary Human T Cells," J Immunother, Oct. 2009; 32(8): pp. 1-19.

Y. Nakazawa et al., "PiggyBac-mediated Cancer Immunotherapy Using EBV-specific Cytotoxic T-cells Expressing HER2-specific Chimeric Antigen Receptor," Mol Ther. Dec. 2011, 19(12): 2133-2143 (pp. 1-11).

Y. Nakazawa et al., "Optimization of the PiggyBac Transposon System for the Sustained Generic Modification of Human T-Lymphocytes," J Immunother. Oct. 2009 ; 32(8): pp. 1-18.

Y. Nakazawa et al., "Evaluation of long-term transgene expression in piggyBac modified human T lymphocytes," J Immunother. Jan. 2013; 36(1): pp. 1-16.

M. H. Huls et al., "Clinical Application of Sleeping Beauty and Artificial Antigen Presenting Cells to Genetically Modify T Cells from Peripheral and Umbilical Cord Blood," J Vis Exp. Feb. 2013, 1;(72):e50070, p. 1-8.

International Search Report dated Dec. 27, 2016, issued for PCT/JP2016/079989.

Office Action dated Sep. 24, 2021, issued for CN patent application 201680058705.6 and English translation thereof.

* cited by examiner

METHOD FOR PREPARING GENETICALLY-MODIFIED T CELLS WHICH EXPRESS CHIMERIC ANTIGEN RECEPTOR

TECHNICAL FIELD

The present invention relates to a method for preparing genetically-modified T cells which express chimeric antigen receptor, and uses therefor. The present application claims priority based on Japanese Patent Application No. 2015-200458 filed on Oct. 8, 2015 and the content of the patent application is hereby incorporated by reference herein in its entirety.

BACKGROUND ART

Gene-modified T-cell therapy (CAR therapy) using a chimeric antigen receptor (hereinafter may be referred to as "CAR") find more and more clinical application. A CAR typically has a structure composed of a single chain variable region of an antibody as the extracellular domain, to which linked are a transmembrane region, CD3ξ, and an intracellular domain of a molecule which transmits costimulatory signals. The CAR-T cells are activated by binding to the antigen according to specificity of the antibody, and injures the target cells (for example, cancer cells). CAR therapy has advantages such as relatively easy cell preparation, high cytotoxic activity, and sustainable effect, and thus is expected as a new treatment means for refractory subjects and subjects having resistance to conventional therapy. In the actual clinical trials carried out in Europe and the United States, the CAR for the CD19 antigen expressed on the cell surface was gene-introduced into the peripheral blood T-cells collected from patients with chemotherapy-resistant acute lymphoblastic leukemia, cultured, and infused; satisfactory results with a remission rate of 80 to 90% was reported (Grupp S A et al., N Engl J Med, 368(16): 1509-18. 2013; Maude S L et al., N Engl J Med, 371(16): 1507-17.2014; Lee D W et al., Lancet. 2015 Feb. 7; 385(9967): 517-28). In the United States, CAR therapy has been attracting attention as one of the most promising therapies for refractory cancer.

In prior art, the cells used in CAR therapy (CAR-T cells) are prepared using viral vectors. However, the commonly used retroviruses have problem of safety, because the frequency of insertion mutation to proto-oncogene is high (leukemia frequently occurs in gene therapy using hematopoietic stem cells). In addition, in the prior art method, cell lines and fetal bovine serum are used for culturing, so that there is a fear about long-term safety particularly in pediatric patients. Furthermore, the use of a viral vector requires special equipment for cell culturing, which highly increases the treatment cost and causes problem of cost efficiency (Non-Patent Literature 4).

CITATION LIST

Non Patent Literature

[NPL 1] Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med, 368(16):1509-18. 2013

[NPL 2] Maude S L, Frey N, Shaw P A, Aplenc R, Barrett D M, Bunin N J, Chew A, Gonzalez V E, Zheng Z, Lacey S F, Mahnke Y D, Melenhorst J J, Rheingold S R, Shen A, Teachey D T, Levine B L, June C H, Porter D L, Grupp S A. Chimeric antigen receptor T cells for sustained remissions in leukemia. N Engl J Med, 371(16):1507-17. 2014

[NPL 3] Lee D W, Kochenderfer J N, Stetler-Stevenson M, Cui Y K, Delbrook C, Feldman S A, Fry T J, Orentas R, Sabatino M, Shah N N, Steinberg S M, Stroncek D, Tschernia N, Yuan C, Zhang H, Zhang L, Rosenberg S A, Wayne A S, Mackall C L. T cells expressing CD19 chimeric antigen receptors for acute lymphoblastic leukaemia in children and young adults: a phase 1 dose-escalation trial. Lancet. 2014

[NPL 4] Morgan R A. Faster, cheaper, safer, T-cell engineering. J Immunother, 36(1):1-2. 2013

SUMMARY OF INVENTION

Technical Problem

In order to solve the problems in prior art CAR therapy using a viral vector, the use of a transposon method, which is one of genetic modification techniques using a non-viral vector, has been studied. A transposon method allows lasting gene introduction as in the case of a viral vector technique, but has problems that the gene introduction efficiency by a transposon method is lower than a viral vector method, and the cells are damaged by the gene introduction operations (for example, electroporation and its improvement method), and the cell survival rate and the cell proliferation rate decrease. The objects of the present invention are to solve these problems, and contribute to the improvements of clinical application and treatment results of CAR therapy.

Solution to Problem

The inventors eagerly studied to solve the above-described problems. As a result of this, it was found that co-culturing of the T cells after gene introduction operation (genetically-modified T cells) with the separately prepared activated T cells improved the gene introduction efficiency and the survival rate/proliferation rate, and increased the number of the finally obtained CAR-T cells. On the other hand, efficient preparation of virus-specific CAR-T cells was achieved by the strategy of co-culturing of the T cells after gene introduction operation (genetically-modified T cells) with activated T cells holding a viral peptide. The invention described below is based on mainly these results.

[1] A method for preparing genetically-modified T cells expressing chimeric antigen receptor, including the following steps (1) to (4):

(1) a step of preparing non-proliferative cells which are obtained by stimulating a group of cells including T cells using an anti-CD3 antibody and an anti-CD28 antibody followed by a treatment for causing the cells to lose their proliferation capability;

(2) a step of obtaining genetically-modified T cells into which a target antigen-specific chimeric antigen receptor gene has been introduced using a transposon method;

(3) a step of mixing the non-proliferative cells prepared by step (1) with the genetically-modified T cells obtained by step (2), and co-culturing the mixed cells while stimulating the mixed cells using an anti-CD3 antibody and anti-CD28 antibody; and (4) a step of collecting the cells after culture.

[2] The preparation method according to [1], wherein a step of culturing the cells after the co-culturing in the presence of a T-cell growth factor is carried out between step (3) and step (4).

[3] The preparation method according to [1] or [2], wherein the period of the co-culturing in step (3) is one day to 14 days.

[4] The preparation method according to any one of [1] to [3], wherein step (3) is carried out in the presence of a T-cell growth factor.

[5] The preparation method according to [4], wherein the T-cell growth factor is IL-15.

[6] The preparation method according to [4], wherein the T-cell growth factor is a combination of IL-15 and IL-7.

[7] A method for preparing genetically-modified T cells expressing chimeric antigen receptor, including the following steps (i) to (iv):

(i) a step of preparing non-proliferative cells holding a viral peptide antigen, which are obtained by stimulating a group of cells including T cells using an anti-CD3 antibody and an anti-CD28 antibody followed by culturing in the presence of the viral peptide antigen and a treatment for causing the cells to lose their proliferation capability;

(ii) a step of obtaining genetically-modified T cells into which a target antigen-specific chimeric antigen receptor gene has been introduced using a transposon method;

(iii) a step of mixing the non-proliferative cells prepared by step (i) with the genetically-modified T cells obtained by step (ii), and co-culturing the mixed cells; and (iv) a step of collecting the cells after culture.

[8] The preparation method according to [7], wherein a step of culturing the cells after the co-culturing in the presence of a T-cell growth factor is carried out between step (iii) and step (iv).

[9] The preparation method according to [7] or [8], wherein the period of the co-culturing in step (iii) is one day to 14 days.

[10] The preparation method according to any one of [7] to [9], wherein step (iii) is carried out in the presence of a T-cell growth factor.

[11] The preparation method according to [10], wherein the T-cell growth factor is IL-15.

[12] The preparation method according to [10], wherein the T-cell growth factor is a combination of IL-15 and IL-7.

[13] The preparation method according to any one of [1] to [12], wherein the group of cells including T-cells is peripheral blood mononuclear cells (PBMCs).

[14] The preparation method according to any one of [1] to [13], wherein the treatment for losing the proliferation capability is irradiation.

[15] The preparation method according to any one of [1] to [14], wherein the transposon method is the PiggyBac transposon method.

[16] The preparation method according to any one of [1] to [15], wherein the target antigen is the CD19, GD2, GMCSF receptor or the IGF receptor.

[17] The preparation method according to any one of [1] to [16], wherein the non-proliferative cells and the genetically-modified T cells are derived from an identical individual.

[18] Genetically-modified T cells expressing chimeric antigen receptor obtained by the preparation method according to any one of [1] to [17].

[19] A cell preparation including the genetically-modified T cells according to [18] in a therapeutically effective amount.

[20] A cancer therapy including a step of administering a therapeutically effective amount of the genetically-modified T cells according to [18] to a cancer patient.

DESCRIPTION OF EMBODIMENTS

Figure 1:
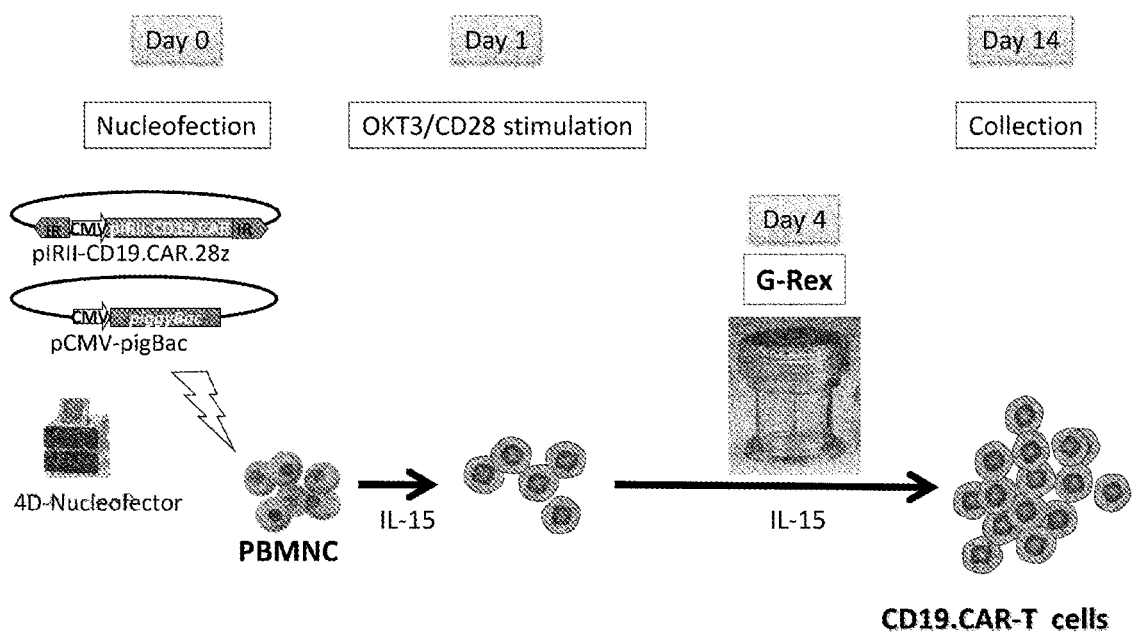
FIG. 1 depicts preparation and culturing of CAR-T cells by a prior art method (culturing method 1).

The present invention relates to a method for preparing genetically-modified T cells (CAR-T cells) expressing chimeric antigen receptor. The CAR-T cells obtained by the preparation method of the present invention may be used in a CAR therapy. The present invention provides generally two preparation methods, more specifically, a method including co-culturing with activated T cells (for convenience of explanation, the method may be referred to as "the first preparation method"), and a method including co-culturing with activated T cells holding a viral peptide (for convenience of explanation, the method may be referred to as "the second preparation method"). Unless otherwise specified, the cells (for example, T cells) in the present description are human cells.

1. Method Including Co-Culturing with Activated T Cells

In this preparation method (the first preparation method), the following steps (1) to (4) are carried out:

(1) a step of preparing non-proliferative cells which are obtained by stimulating a group of cells including T cells using an anti-CD3 antibody and an anti-CD28 antibody followed by a treatment for causing the cells to lose their proliferation capability;

(2) a step of obtaining genetically-modified T cells into which a target antigen-specific chimeric antigen receptor gene has been introduced using a transposon method;

(3) a step of mixing the non-proliferative cells prepared by step (1) with the genetically-modified T cells obtained by step (2), and co-culturing the mixed cells while stimulating the mixed cells using an anti-CD3 antibody and anti-CD28 antibody; and (4) a step of collecting the cells after culture.

Step (1) is a step of obtaining non-proliferative cells used for the protection of the T cells after gene introduction operation (the genetically-modified T cells used in step (2)); firstly, a group of cells including T cells is stimulated with an anti-CD3 antibody and an anti-CD28 antibody. Through this treatment, activated T cells are obtained. As the "a group of cells including T cells", preferably, PBMCs (peripheral blood mononuclear cells) collected from the peripheral blood are used. The "group of cells including T cells" herein may be, for example, the PBMCs which have been purified to increase the T-cell content, or mononuclear cells collected from the peripheral blood by pheresis.

For example, the T cells in a group of cells can be stimulated with an anti-CD3 antibody and an anti-CD28 antibody by culturing them in a culture vessel (for example, culture dish) coated with an anti-CD3 antibody and an anti-CD28 antibody on the culturing surface for three hours to three days, preferably six hours to two days, and more preferably from 12 hours to one day. The anti-CD3 antibody (for example, the trade name CD3pure antibody provided by Miltenyi Biotec may be used) and the anti-CD28 antibody (for example, the trade name CD28pure antibody provided by Miltenyi Biotec may be used) are commercially available and are easily available. The stimulation in step (1) may be carried out using the magnetic beads coated with an anti-CD3 antibody and an anti-CD28 antibody (for example, Dynabeads T-Activator CD3/CD28 provided by VERITAS). The anti-CD3 antibody is preferably "OKT3" clone.

The cells stimulated with an anti-CD3 antibody and an anti-CD28 antibody are subjected to a treatment for causing them to lose their proliferation capability, preferably after culturing in the presence of a T-cell growth factor. This culturing increases the activity of the cells after the stimulation treatment. The period of the culture is, for example, from one day to 10 days, preferably from two days to seven days, and more preferably from three days to four days. If the culture period is too short, sufficient activation cannot be obtained, and if the culture period is too long, attenuation of the costimulatory molecule may occur. The cells after culture may be once subjected to cryopreservation. In this case, the cells are unfrozen before use, stimulated with the anti-CD3 antibody and the CD28 antibody again (the conditions are the same as described above), and then subjected to "the treatment for losing the proliferation capability".

Through the "treatment for losing the proliferation capability", the activated T cells having no proliferation capability (non-proliferative cells) are obtained. The treatment for losing the proliferation capability is typically irradiation, but may use a drug. The irradiation is carried out by, for example, using a γ-ray, at an intensity of 25 Gy to 50 Gy, for 15 to 30 minutes.

In the step (2), genetically-modified T cells in which a target antigen-specific chimeric antigen receptor gene has been introduced are obtained. Namely, in the present invention, a CAR gene is introduced to T cells, thereby CAR-T cells are obtained. The gene introduction is preferably carried out by a transposon method. The transposon method is one of the non-viral gene introduction methods. Transposon is the generic name of short gene sequences causing a gene transposition conserved during the process of evolution. A pair of a gene enzyme (transposase) and its specific recognition sequence causes gene transposition. The transposon method may be, for example, the piggyBac transposon method. The piggyBac transposon method uses the transposon isolated from insects (Fraser M J et al., Insect Mol Biol. 1996 May; 5(2): 141-51; Wilson M H et al., Mol Ther. 2007 January; 15(1): 139-45), and allows highly efficient integration into mammal chromosomes. The piggyBac transposon method is actually used for the introduction of the CAR gene (for example, see Nakazawa Y, et al., J Immunother 32: 826-836, 2009; Nakazawa Y et al., J Immunother 6: 3-10, 2013). The transposon method applicable to the present invention is not limited to that using piggyBac, and may use a method using transposon, for example, Sleeping Beauty (Ivics Z, Hackett P B, Plasterk R H, Izsvak Z (1997) Cell 91: 501-510), Frog Prince (Miskey C, Izsvak Z, Plasterk R H, Ivics Z (2003) Nucleic Acids Res 31: 6873-6881), Toll (Koga A, Inagaki H, Bessho Y, Hori H. Mol Gen Genet. 1995 Dec. 10; 249 (4): 400-5; Koga A, Shimada A, Kuroki T, Hori H, Kusumi J, Kyono-Hamaguchi Y, Hamaguchi S. J Hum Genet. 2007; 52(7): 628-35. Epub 2007 Jun. 7), Tol2 (Koga A, Hori H, Sakaizumi M (2002) Mar Biotechnol 4: 6-11; Johnson Ha mL et M R, Yergeau D A, Kuliyev E, Takeda M, Taira M, Kawakami K, Mead P E (2006) Genesis 44: 438-445; Choo B G, Kondrichin I, Parinov S, Emelyanov A, Go W, Toh W C, and Korzh V (2006) BMC Dev Biol 6: 5).

The introduction operation by the transposon method may be carried out by an ordinary method with reference to past literatures (for example, for the piggyBac transposon method, see Nakazawa Y, et al., J Immunother 32: 826-836, 2009, Saha S, Nakazawa Y, Huye L E, Doherty J E, Galvan D L, Rooney C M, Wilson M H. J Vis Exp. 2012 Nov. 5; (69): e423). In a preferred embodiment of the present invention, the piggyBac transposon method is used. Typically, in the piggyBac transposon method, a vector including the gene coding piggyBac transposase (transposase plasmid) and a vector having a structure wherein the gene coding a target protein (CAR gene) is sandwiched between piggyBac inverted repeat sequences (transposon plasmid) are prepared, and these vectors are introduced (transfected) to the target cell. The transfection may use various methods such as electroporation, nucleofection, lipofection, or calcium phosphate method.

Examples of cell into which the CAR gene is introduced (a target cell) include CD4-positive CD8-negative T-cells, CD4-negative CD8-positive T-cells, T-cells prepared from iPS cells, αβ-T-cells, and γδ-T-cells. Various cell populations may be used, as long as they contain the above-described T cells or precursor cells. PBMCs (peripheral blood mononuclear cells) collected from the peripheral blood is one of the preferred target cells. More specifically, in a preferred embodiment, gene introduction operation is carried out on the PBMCs. The PBMCs may be prepared by an ordinary method. The method for preparing the PBMCs may refer to, for example, Saha S, Nakazawa Y, Huye L E, Doherty J E, Galvan D L, Rooney C M, Wilson M H. J Vis Exp. 2012 Nov. 5; (69): e4235.

The cells after the gene introduction operation is subjected to the co-culturing in step (3). Before step (3), the cells after the gene introduction operation may be cultured in the presence of a T-cell growth factor (for example, IL-15 or IL-7).

The CAR gene codes the chimeric antigen receptor (CAR) recognizing a specific target antigen. The CAR is a structural body including an extracellular domain specific to the target, a transmembrane domain, and an intracellular signal domain for the effector function of immunocytes. These domains are explained below.

(a) Extracellular Domain

The extracellular domain specifically binds to the target. For example, the extracellular domain contains the scFv fragment of the anti-target monoclonal antibody. Examples of the monoclonal antibody used herein include rodent antibodies (e.g., mouse, rat, and rabbit antibodies), human antibodies, and humanized antibodies. The humanized monoclonal antibody is prepared by making the structure of the monoclonal antibody of any animal species (for example, mice or rats) analogous to the structure of the human antibody, and includes the human type chimera antibody, which is prepared by substituting only the constant region of an antibody with that of the human antibody, and the human type CDR-grafted antibody, which is prepared by substituting the parts excluding the CDR (complementary determining region) in the constant and variable regions with those of the human antibody (P. T. Johons et al., Nature 321, 522 (1986)). For the purpose of increasing the antigen binding activity of human type CDR-grafted antibodies, already developed are the improvement techniques for the method for choosing a human antibody framework (FR) having high homology for mouse antibodies, the method for preparing humanized antibodies having high homology, and the method for transplanting a mouse CDR in a human antibody, followed by substitution of amino acids in the FR region (e.g., U.S. Pat. Nos. 5,585,089, 5,693,761, 5,693,762, 6,180,370, European Patent Application No. 451216, European Patent Application No. 682040, and Japanese Patent No. 2828340), which can be used for the preparation of humanized antibodies.

The scFv fragment is a structural body wherein the light chain variable region (VL) and heavy chain variable region (VH) of immunoglobulin are linked through a linker, and retains binding ability for the antigen. The linker may be, for example, a peptide linker. The peptide linker is composed of a peptide made by linear linking of amino acids. Typical examples of the peptide linker are the linkers composed of glycine and serine (GGS and GS linkers). The amino acids composing the GGS and GS linkers, glycine and serine, are small in their sizes, and thus hardly form higher-order structures. The length of the linker is not particularly limited. For example, a linker having 5 to 25 amino acid residues may be used. The number of the amino acid residue composing the linker is preferably from 8 to 25, and more preferably from 15 to 20.

The target used herein is typically an antigen which shows specific expression in tumor cells. The "specific expression" means significant or remarkable expression in comparison with the cells other than tumor, and will not intend to confine to those showing no expression in the cells other than tumor. Examples of the target antigen include the CD19 antigen, CD20 antigen, GD2 antigen, CD22 antigen, CD30 antigen, CD33 antigen, CD44 variant 7/8 antigen, CEA antigen, Her2/neu antigen, MUC1 antigen, MUC4 antigen, MUC6 antigen, IL-13 receptor-alpha 2, immunoglobulin light chain, PSMA antigen, and VEGF receptor 2.

The GM-CSF (granulocyte macrophage colony-stimulating factor) receptor expressed in leukemic stem cells/precursor cells may be used as the target. In this case, GM-CSF, which is a ligand of the GM-CSF receptor, is used as the extracellular domain composing CAR. The leukemia stem cells, leukemia precursor cells, leukemia cells and others of bone marrow tumor are used as the targets of the CAR-T cells, whereby the cells applicable to prevention and treatment of myeloproliferative tumor, myelodysplastic/myeloproliferative tumor (CMML, JMML, CML, MDS/MPN-UC), myelodysplastic syndrome, acute myelogenous leukemia, and the like are prepared.

(b) Transmembrane Domain

The transmembrane domain intervenes between the extracellular domain and intracellular signal domain. Examples of the transmembrane domain used herein include CD28, CD3E, CD8a, CD3, CD4, and 4-1BB. Alternatively, a transmembrane domain composed of an artificially constructed polypeptide may be used.

(c) Intracellular Signal Domain

The intracellular signal domain transmits the signals necessary for exertion of the effector function of immunocytes. More specifically, when the extracellular domain binds with the target antigen, an intracellular signal domain capable of transmitting the signals necessary for activation of immunocytes are used. The intracellular signal domain includes the domain for transmitting the signals through the TCR complex (for convenience, referred to as "the first domain"), and the domain for transmitting the costimulatory signals (for convenience, referred to as "the second domain"). As the first domain, CD3ξ or other intracellular domains such as FcεRIγ may be used. The use of CD3ξ is preferred. As the second domain, the intracellular domain of a costimulatory molecule is used. Examples of the costimulatory molecule include CD28, 4-1BB (CD137), CD2, CD4, CD5, CD134, OX-40, and ICOS. The use of the intracellular domain of CD28 or 4-1BB is preferred.

The linking form of the first and second domains is not particularly limited, and preferably the second domain is disposed on the transmembrane domain side, because it is known that co-stimulation was strongly transmitted when CD3ξ was linked distally in a past case. The same or different kinds of plural intracellular domains may be linked in tandem to form the first domain. The same holds true for the second domain.

The first and second domains may be directly linked, or a linker may intervene between them. The linker may be, for example, a peptide linker. The peptide linker is composed of peptides which are linear chains of amino acids. The structure and characteristics of the peptide linker are as described above. However, the linker used herein may be composed solely of glycine. The length of the linker is not particularly limited. For example, a linker composed of 2 to 15 amino acid residues may be used.

(d) Other Elements

A leader sequence (signal peptide) is used to promote CAR secretion. For example, the leader sequence of the GM-CSF receptor may be used. In addition, the structure is preferably composed of an extracellular domain and a transmembrane domain linked together through a spacer domain. More specifically, the CAR according to a preferred embodiment contains a spacer domain between the extracellular domain and transmembrane domain. The spacer domain is used for promoting linking between the CAR and target antigen. For example, the Fc fragment of a human IgG (for example, human IgG1 or human IgG4) may be used as the spacer domain. Alternatively, a part of the extracellular domain of CD28 or a part of the extracellular domain of CD8a may be used as the spacer domain. A spacer domain may be placed between the transmembrane domain and intracellular signal domain.

There are some reports on the experiments and clinical studies using CARs (for example, Rossig C, et al. Mol Ther 10: 5-18, 2004; Dotti G, et al. Hum Gene Ther 20: 1229-1239, 2009; Ngo M C, et al. Hum Mol Genet 20 (R1): R93-99, 2011; Ahmed N, et al. Mol Ther 17: 1779-1787, 2009; Pule M A, et al. Nat Med 14: 1264-1270, 2008; Louis C U, et al. Blood 118: 6050-6056, 2011; Kochenderfer J N, et al. Blood 116: 4099-4102, 2010; Kochenderfer J N, et al. Blood 119: 2709-2720, 2012; Porter D L, et al. N Engl J Med 365: 725-733, 2011; Kalos M, et al. Sci Transl Med 3: 95ra73, 2011; Brentjens R J, et al. Blood 118: 4817-4828, 2011; and Brentjens R J, et al. Sci Transl Med 5: 177 ra38, 2013), and the CARs in the present invention may be constructed with reference to these reports.

In the transposon plasmid, a poly-A additional signal sequence is disposed down stream of the CAR gene. Transcription is terminated by the use of the poly-A additional signal sequence. The poly-A additional signal sequence may be, for example, the poly-A additional sequence of SV40, or the poly-A additional sequence of a bovine-derived growth hormone gene.

The transposon plasmid may include, for example, a gene for detection (for example, a reporter gene, cell or tissue-specific gene, or selectable marker gene), an enhancer sequence, and a WRPE sequence. The gene for detection is used for the judgement of success/failure or efficiency of the introduction the expression cassette, detection of CAR expression or judgement of the expression efficiency, and selection and collection of the cells having expressed the CAR gene. On the other hand, the enhancer sequence is used for improving the expression efficiency. Examples of the gene for detection include the neo gene imparting resistance against neomycin, the npt gene (Herrera Estrella, EMBO J. 2 (1983), 987-995) and npt II gene (Messing & Vierra. Gene 1 9: 259-268(1982)) imparting resistance against kanamycin, the hph gene imparting resistance against hygromycin (Blochinger & Diggl mann, Mol Cell Bio 4: 2929-2931), and the dhfr gene imparting resistance against Methotrexate (Bourouis et al., EMBO J. 2 (7)) (the aforementioned are marker genes); genes of fluorescence proteins such as the luciferase gene (Giacomin, P1. Sci. 116 (1996), 59 to 72; Scikantha, J. Bact. 178 (1996), 121), the β-glucuronidase (GUS) gene, GFP (Gerdes, FEBS Lett. 389 (1996), 44-47), and their variants (EGFP and d2EGFP) (the aforementioned are reporter genes); and the epidarmal growth factor receptor (EGFR) gene deficient in the intracellular domain. The gene for detection is linked to the CAR gene through, for example, a bicistronic control sequence (for example, internal ribosome entry site (IRES)) and a sequence coding a self cleavage peptide. Examples of the self cleavage peptide include, but not limited to, the 2A peptide (T2A) derived from Thosea asigna virus. Known examples of the self cleavage peptide include the 2A peptide (F2A) defived from the Foo-and-mouse disease virus (FMDV), the 2A peptide (E2A) defived from equine rhinitis A virus (ERAV), and the 2A peptide (P2A) defived from porcine teschovirus (PTV-1).

In step (3), the non-proliferative cells prepared in step (1) and the genetically-modified T cells obtained in step (2) are mixed, and the mixed cells are co-cultured while stimulating the mixed cells using an anti-CD3 antibody and an anti-CD28 antibody. As a result of this, stimulation through the costimulatory molecules by the non-proliferative cells and stimulation by an anti-CD3 antibody and an anti-CD28 antibody are added, whereby the genetically-modified T cells are activated, and their survival and proliferation are promoted.

The ratio between the number of the non-proliferative cells used for co-culturing and the number of the genetically-modified T cells (the number of the non-proliferative cells/the number of genetically-modified T cells) is not particularly limited, and, for example, from 0.025 to 0.5.

In oder to improve the survival rate/proliferation rate of the cells, it is preferred to use a culture solution containing a T-cell growth factor in the activation treatment. The T-cell growth factor is preferably IL-15. Preferably, a culture solution containing IL-15 and IL-7 is used. The concentration of IL-15 is, for example, from 5 ng/mL to 10 ng/mL. The concentration of IL-7 is, for example, from 5 ng/mL to 10 ng/mL. The T-cell growth factor such as IL-15 or IL-7 may be prepared according to a common procedure. Alternatively, a commercial product may be used. Although the use of animal T-cell growth factors other than human ones will not be excluded, the T-cell growth factor used herein is usually derived from human (may be a recombinant). The growth factors such as human IL-15 and human IL-7 are readily available (for example, provided by Miltenyi Biotec, R&D systems).

A culture medium containing blood serum (for example, human blood serum or fetal bovine serum) may be used, but the use of a serum-free medium allows the preparation of cells having advantages of high safety in clinical application, and little difference in the culture efficiency among blood serum lots. Specific examples of the serum-free medium for T cells include TexMACS™ (Miltenyi Biotec) and AIM V (registered trademark) (Thermo Fisher Scientific). When a blood serum is used, the blood serum is preferably a self-blood serum, or a blood serum collected from the individual who is the origin of the genetically-modified T cells obtained in step (2) (typically, the patient to receive administration of the chimeric antigen receptor genetically-modified T cells obtained by the preparation method of the present invention). The basal culture medium is the one suitable for culture of T cells, and specific examples include the above-listed TexMACS™ and AIM V (registered trademark). Other culture conditions may be common ones, as long as they are suitable for the survival and proliferation of T cells. For example, the culture is carried out in a $CO_2$ incubator adjusted at 37° C. ($CO_2$ concentration: 5%). The stimulation by an anti-CD3 antibody and an anti-CD28 antibody is the same as that in step (1), so the explanations thereof are omitted.

The period of the co-culturing in step (3) is, for example from one day to 10 days, preferably from one day to seven days, and more preferably two days to four days. If the culture period is too short, sufficient effect cannot be obtained, and if the culture period is too long, the activity (vital force) of the cells may decrease.

In step (4) following step (3), the cells after culture are collected. The collection operation may use an ordinary method. For example, the collection is carried out by pipetting or centrifugation treatment.

In a preferred embodiment, the cells after the co-culturing are cultured in the presence of a T-cell growth factor between step (3) and step (4). This step allows efficient cell expansion, and also improves the survival rate of cells.

The T-cell growth factor may be, for example, IL-15 or IL-7. Preferably, in the same manner as in step (3), the cells are cultured on a medium containing IL-15 and IL-7. The culture period is, for example, from one day to 21 days, preferably from five days to 18 days, and more preferably from 10 days to 14 days. If the culture period is too short, the number of cells will not increase sufficiently, and if the culture period is too long, the activity (vital force) of the cells may decrease, and the cells may be exhausted or fatigued. The cells may be subcultured during culturing. Additionally, the culture medium is replaced as necessary during culturing. For example, about ⅓ to ⅔ of the culture solution is replaced with a new culture medium once every three days.

2. Method Including Co-Culturing with T Cells Holding Viral Peptide

Another embodiment (second preparation method) of the present invention relates to a method for preparing a virus specific chimeric antigen receptor genetically-modified T cells (hereinafter referred to as "virus-specific CAR-T cells"). The virus-specific CAR-T cells have important advantages in clinical application, such as their use in autotransplantation improves internal persistence by stimulation from a viral T cell receptor, and their use in allogeneic transplantation further allows the preparation of CAR-T from a transplanted donor owing to the reduction of allogeneic immunity reaction (GVHD), and creates possibility of drug formulation of CAR-T cells from a third party donor. Actually, there is a report that virus-specific CAR-T cells survice longer in the body (Pule M A, et al. Nat Med. 2008 November; 14 (11): 1264-70). In addition, the report of a third party-derived EBV-specific CTL clinical study (Annual Review Blood 2015, published in January 2015, Chugai-Igakusha) supports high level of safety of virus-specific cytotoxic T cells (CTLs).

The preparation method of this embodiment includes the following steps (i) to (iv). The items not referred herein (for example, the method for preparing a group of cells including T cells, basic operation of stimulation by an anti-CD3 antibody and an anti-CD28 antibody, the method of the treatment for losing proliferation capability, the operation of gene introduction by a transposon method, basic operation of co-culturing, and the method for collecting cells) are the same as those in the above-described first preparation method, so that repetitive description thereof will be omitted, and corresponding explanation is incorporated.

(i) A step of preparing non-proliferative cells holding a viral peptide antigen, which are obtained by stimulating a group of cells including T cells using an anti-CD3 antibody and an anti-CD28 antibody followed by culturing in the presence of the viral peptide antigen and a treatment for causing the cells to lose their proliferation capability (ii) A step of obtaining genetically-modified T cells into which a target antigen-specific chimeric antigen receptor gene has been introduced using a transposon method (iii) A step of mixing the non-proliferative cells prepared by step (i) with the genetically-modified T cells obtained by step (ii), and co-culturing the mixed cells (iv) A step of collecting the cells after culture.

In step (i), firstly, the group of cells including T cells are stimulated with an anti-CD3 antibody and an anti-CD28 antibody, thereby obtaining activated T cells. Thereafter, the cells are subjected to culturing in the presence of the viral peptide antigen and a treatment for causing the cells to lose their proliferation capability. As a result of this, non-proliferative "activated T cells holding a viral peptide antigen on the cell surface" (hereinafter referred to as "viral peptide-holding non-proliferative cells") are obtained. The order of culturing in the presence of the viral peptide antigen and a treatment for causing the cells to lose their proliferation capability is not particularly limited. Accordingly, the proliferation capability may be lost after culturing in the presence of the viral peptide antigen, or the cells may be cultured in the presence of the viral peptide antigen after they were caused to lose their proliferation capability. Preferably, the former order is adopted in the expectation that the intake of the viral peptide antigen would be better than before the loss of proliferation capability. In order to culture the cells in the presence of the viral peptide antigen, for example, a culture medium containing the viral peptide antigen is used. Alternatively, the viral peptide antigen may be added to the culture medium during culturing. The addition concentration of the viral peptide antigen is, for example, from 0.5 µg/mL to 1 µg/mL. The culture period is, for example, from 10 minutes to 5 hours, and preferably from 20 minutes to 3 hours. The "viral peptide antigen" in the present description means an epitope peptide or a long peptide containing an epitope which can induce cytotoxic T cells (CTLs) specific to a specific virus. Examples of the viral peptide antigen include, but not limited to, antigen peptides of adenovirus (AdV) (for example, see WO 2007015540 A1), antigen peptides of cytomegalovirus (CMV) (for example, see Japanese Unexamined Patent Application Publication No. 2002-255997, Japanese Unexamined Patent Application Publication No. 2004-242599, and Japanese Unexamined Patent Application Publication No. 2012-87126), and antigen peptides of Epstein-Barr virus (EBV) (for example, see WO 2007049737 A1, Japanese Patent Application No. 2011-177487, and Japanese Unexamined Patent Application Publication No. 2006-188513). The viral peptide antigen can be prepared by a common procedure (for example, a solution-phase synthesis method or a solid-phase synthesis method) based on the sequence information. Some viral peptide antigens are commercially available (for example, provided by Medical & Biological Laboratories Co., Ltd., Takara Bio, Inc., and Miltenyi Biotec).

One antigen peptide may be used, but usually two or more antigen peptides (an antigen peptide mixture) are used. For example, an AdV antigen peptide mixture, a CMV antigen peptide mixture, or an EBV antigen peptide mixture, or a combination of two or more of these antigen peptide mixtures (for example, a mixture of the AdV antigen peptide mixture, CMV antigen peptide mixture, and EBV antigen peptide mixture) is used. The combination of two or more antigen peptides allows obtainment of plural activated T cells having different targets (antigen peptides), which would increase the subjects (patients) to whom the CAR-T cells obtained by the preparation method of the present invention is effective (the improvement of cover rate). When determining which virus the antigen peptide to be used is derived from, the use of the CAR-T cells obtained by the preparation method of the present invention, specifically the disease and the disease state of the patient to be treated may be considered. For example, when the treatment of recurrent leukemia after transplantation of hematopoietic stem cells is aimed at, it is suggested that the antigen peptide mixture of EBV virus be used alone or in combination with other viral antigen peptide mixture. The AdV antigen peptide mixture, CMV antigen peptide mixture, and EBV antigen peptide mixture are commercially available (for example, PepTivator (registered trademark) AdV5 Hexon, PepTivator (registered trademark) CMV pp65, PepTivator (registered trademark) EBV EBNA-1, PepTivator (registered trademark), and EBV BZLF1 provided by Miltenyi Biotec, and Pep- Mix™ Collection HCMV, PepMix™ EBV (EBNA1) provided JPT Peptide Technologies, and the like) are easily available.

Step (ii) is the same as step (2) in the above-described first preparation method of the present invention. Through this step, the genetically-modified T cells (CAR-T cells) are obtained.

In step (iii), the non-proliferative cells (viral peptide-holding non-proliferative cells) prepared in step (i) and the genetically-modified T cells obtained in step (ii) are mixed, and the mixed cells are co-cultured. As a result of this, stimulation through the costimulatory molecules by the non-proliferative cells and stimulation by the viral antigen peptide are added, whereby the virus antigen specific genetically-modified T cells are activated, and their survival and proliferation are promoted.

The ratio between the number of the non-proliferative cells used for co-culturing and the number of the genetically-modified T cells (the number of non-proliferative cells/the number of genetically-modified T cells) is not particularly limited, and, for example, from 0.025 to 0.5.

In this step, in principle, stimulation by an anti-CD3 antibody and an anti-CD28 antibody is not applied for the purposes of, for example, selectively proliferating the virus-specific CAR-T cells, or preventing exhaustion and fatigue of the T cells by avoiding strong stimulation. On the other hand, in order to increase the survival rate/proliferation rate of the cells, it is preferred that a culture solution containing a T-cell growth factor be used during the co-culturing. The T-cell growth factor is preferably IL-15. Preferably, a culture solution containing IL-15 and IL-7 are used. The addition amount of IL-15 is, for example, from 5 ng/mL to 10 ng/mL. In the same manner, the addition amount of IL-7 is, for example, from 5 ng/mL to 10 ng/mL. The conditions not referred herein (for example, possibility of the use of the blood serum, the basal culture medium, and the incubation temperature) are the same as those in step (3) of the above-described first preparation method of the present invention.

The viral peptide-holding non-proliferative cells may be added during step (iii). Alternatively, the co-cultured cells are collected, mixed with the viral peptide-holding non-proliferative cells, and then co-culturing is carried out again. These operations may be repeated twice or more times. In this manner, the improvement of the induction rate of the virus-specific CAR-T cells and the increase of the number of the virus-specific CAR-T cells are expected by carrying out plural times of the stimulation or activation using the viral peptide-holding non-proliferative cells. The viral peptide-holding non-proliferative cells used herein are prepared anew, or a portion of the preserved cells which have been prepared in step (i).

In step (iii), the period of co-culturing is, for example, from one day to 21 days, preferably from five days to 18 days, and more preferably from 10 days to 14 days. If the culture period is too short, sufficient effect cannot be obtained, and if the culture period is too long, the activity (vital force) of the cells may decrease, and the cells may be exhausted or fatigued.

Before the co-culturing with the viral peptide-holding non-proliferative cells, the genetically-modified T cells obtained in step (ii) may be co-cultured with viral peptide-holding non-proliferative PBMCs (peripheral blood mononuclear cells). In this embodiment, the cells obtained by co-culturing the genetically-modified T cells obtained in step (ii) with the viral peptide-holding non-proliferative PBMCs, and the viral peptide-holding non-proliferative cells prepared in step (i) are mixed, and the mixture is co-cultured. The viral peptide-holding non-proliferative PBMCs herein can be prepared by subjecting PBMCs to culturing in the presence of a viral peptide antigen and a treatment for causing them to lose their proliferation capability. Specifically, for example, PBMC isolated from the peripheral blood are irradiated, and then cultured in the presence of a viral peptide antigen, thus obtaining viral peptide-holding non-proliferative PBMCs. The number of blood collection for carrying out the present invention can be reduced by preparing viral peptide-holding non-proliferative PBMCs using a portion of the PBMCs isolated from the peripheral blood obtained by one time of blood collection, and preparing genetically-modified T cells from another portion, which will bring a markedly big advantage in clinical application. In particular, when the viral peptide-holding non-proliferative cells (the cells used for the second step co-culturing) are prepared by carrying out step (i) using the remaining PBMCs, the three kinds of necessary cells, more specifically, the genetically-modified T cells, viral peptide-holding non-proliferative PBMCs used for co-culturing with these cells, and the viral peptide-holding non-proliferative cells used for the second step co-culturing can be prepared by one time of blood collection, which markedly reduces the burden imposed on the patient in the treatment using the CAR-T cells obtained in the present invention.

In step (iv) following step (iii), the cells after culture are collected. In the same manner as in the above-described first preparation method of the present invention, the step of culturing the co-cultured cells in the presence of the T-cell growth factor (expanded culturing) may be carried out between step (iii) and step (iv). For this cell expansion, viral peptide-holding non-proliferative cells may be added, or viral peptide-holding non-proliferative cells may be added during the cell expansion.

3. Genetically-Modified T Cells which Express Chimeric Antigen Receptor and and Uses Thereof A further aspect of the present invention relates to the genetically-modified T cells which express chimeric antigen receptor gene obtained in the preparation method of the present invention (hereinafter referred to as "CAR-T cells of the present invention") and uses thereof. The CAR-T cells of the present invention can be used for treatment, prevention, or improvement of various diseases (hereinafter referred to as "target diseases") to which the CAR therapy is likely effective. Representative examples of the target disease include, but not limited to, cancer. Examples of the target disease include various B-cell lymphoma (follicular lymphoma, diffuse large B-cell lymphoma, mantle cell lymphoma, MALT lymphoma, intravascular B-cell lymphoma, and CD20-positive Hodgkin's lymphoma), myeloproliferative tumor, myelodysplastic/myeloproliferative tumor (CMML, JMML, CML, MDS/MPN-UC), myelodysplastic syndromes, acute myelocytic leukemia, neuroblastoma, brain tumor, Ewing's sarcoma, osteosarcoma, retinoblastoma, small cell lung cancer, melanoma, ovarian cancer, rhabdomyosarcoma, kidney cancer, pancreas cancer, malignant mesothelioma, and prostate cancer. "Treatment" include alleviation (moderation) of symptoms or associated symptoms characteristic to the target diseases, inhibition or retard of deterioration of symptoms. "Prevention" means prevention or retard of development/expression of diseases (disorders) or their symptoms, or decrease of the risk of development/expression. On the other hand, "improvement" means alleviation (moderation), change for the better, amelioration, or healing (containing partial healing).

The CAR-T cells of the present invention may be prepered in the form of a cell preparation. The cell preparation of the present invention contains the CAR-T cells of the present invention in a therapeutically effective amount. For example, $10^4$ to $10^{10}$ cells are contained for one administration (one dose). The cell preparation may contain dimethylsulfoxide (DMSO) or serum albumin for the purpose of cell protection, antibiotics for the purpose of preventing bacterial contamination, and various components for (for example, vitamins, cytokine, growth factors, and steroids) for the purpose of cell activation, proliferation, or inductive differentiation.

The administration route of the CAR-T cells or cell preparation of the present invention is not particularly limited. For example, they are administered by intravenous injection, intraarterial injection, intraportal injection, intradermal injection, hypodermic injection, intramuscular injection, or intraperitoneal injection. Local administration may be used in place of systemic administration. Examples of the local administration include direct injection into the target tissues, body parts, and organs. The administration schedule may be made according to the sex, age, body weight, and pathology of the subject (patient). A single dose or continuous or periodical multiple doses may be used.

EXAMPLES

<Study of Preparation Efficiency and Gene Introduction Efficiency of CAR-T Cells>

The CAR therapy using a transposon method is advantageous especially in terms of safety in comparison with the case using a viral vector. On the other hand, there are problems that the gene introduction efficiency is low, the cells tend to be damaged by the operation during gene introduction (for example, electroporation), and the number of cells to be obtained is small. In order to solve these problems, the following study was carried out.

1. Material
(1) Antibody
Anti-CD3 antibody (Miltenyi Biotec)
Anti-CD28 antibody (Miltenyi Biotec)
(2) Culture Medium
TexMACS (Miltenyi Biotec)
(3) Cytokine
Recombinant human IL-7 (Miltenyi Biotec)
Recombinant human IL-15 (Miltenyi Biotec)
(4) Viral Peptide Mix
PepTivator (registered trademark) CMV pp65-premium grade, human (Miltenyi Biotec)
PepTivator (registered trademark) AdV5 Hexon-premium grade, human (Miltenyi Biotec)
PepTivator (registered trademark) EBV EBNA-1-premium grade, human (Miltenyi Biotec)
PepTivator (registered trademark) EBV BZLF1-premium grade, human (Miltenyi Biotec)
(5) Plasmid
pIRII-CD19CARvector (expressing CAR)
pCMV-piggyBacvector (expressing piggyBac transposase)
(6) Cell Culture Vessel
24-well uncoated tissue culture plate (Falcon)
24-well tissue culture plate (Falcon)
G-Rex10 (Wilson Wolf)

2. Method
(1) Preparation of Activated T Cells (1-1) Preparation of Anti-CD3 Antibody/Anti-CD28 Antibody Coated (Immunized) Plate An anti-CD3 antibody and an anti-CD28 antibody were diluted with PBS to 1 mg/mL, and added to a 24-well uncoated plate at a rate of 0.5 mL/well. The plate is allowed to stand in an incubator at 37° C. for 2 to 4 hours. The PBS that diluted the antibodies is aspirated, and each well is washed once with 1 mL of PBS.

(1-2) Culturing on Anti-CD3 Antibody/Anti-CD28 Antibody Coated Plate

Day 0: The PBMC isolated from the peripheral blood is diluted to $5 \times 10^5$/mL with TexMACS containing 5 ng/mL of IL-15, and dispensed to the anti-CD3 antibody/anti-CD28 antibody coated plate at 2 mL to each well.

Day 1: The cells are transferred to a 24-well tissue culture plate. Half the amount of the culture solution is replaced, and IL-15 is added to 5 ng/mL.

Day 4: IL-15 is added to 5 ng/mL.

Day 7: The cells are collected, dispensed, and cryopreserved.

(1-3) Re-Stimulation of Activated T Cells

Day 0: Cryopreserved cells are unfrozen, washed twice, diluted to $1 \times 10^6$/mL with TexMACS™ containing IL15 at 5 ng/mL, and dispensed to an anti-CD3 antibody/anti-CD28 antibody coated plate at 2 Ml to each well.

Day 3: The cells are collected, and used for CAR-T culturing.

(2) Preparation and Culturing of CAR-T by Prior Art Method (See Culturing Method 1 and FIG. 1)

Figure 4:
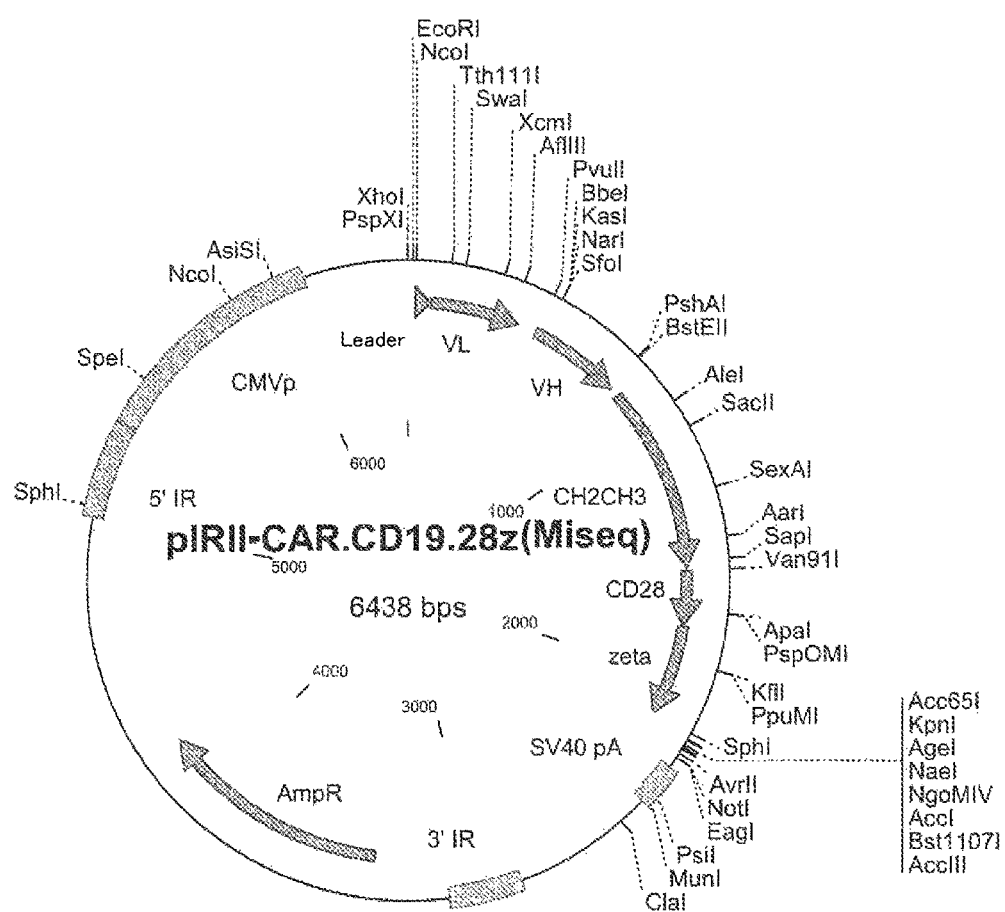
FIG. 4 depicts the structure of the pIRII-CAR.CD19.28z vector (SEQ ID NO. 1), composed of the CD19CAR gene held between the 5' inverted repeat sequence (5'IR) and the 3' inverted repeat sequence (3'IR). CD19CAR includes a reader sequence (SEQ ID NO. 2), a light chain variable region (VL) (SEQ ID NO. 3), a heavy chain variable region (VH) (SEQ ID NO. 4), an Fc region (CH2, CH3) (SEQ ID NO. 5), a transmembrane region of CD28, an intracellular domain (SEQ ID NO. 6), and CD3 (SEQ ID NO. 7).
Figure 5:
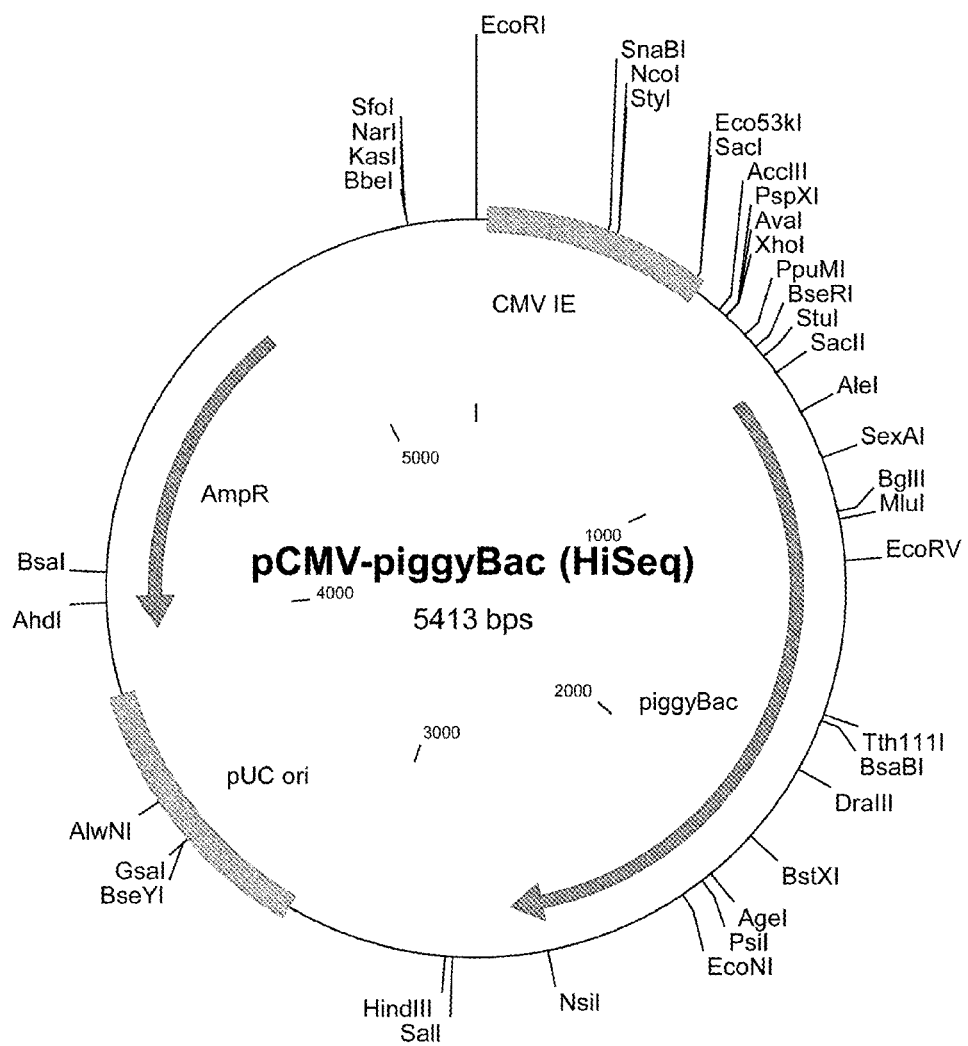
FIG. 5 depicts the structure of the pCMV-pigBac vector (SEQ ID NO. 8), composed of the piggyback transposase gene placed under control of the CMV immediate early promoter.

Day 0: Mononuclear cells are isolated from the peripheral blood, and counted. To $1 \times 10^7$ mononuclear cells, pIRII-CAR.CD19.28z vector (FIG. 4) and pCMV-pigBac vector (FIG. 5) are added in amounts of 5 μg, and the gene is introduced by electroporation (nucleofection) using 4D nucleofector (Lonza). Thereafter, the cells are floated in TexMACS™ containing 10 ng/mL of IL-7 and 5 ng/mL of IL15, and culturing is started on a 24-well plate in an incubator at 37° C.

Day 1: The cells are stimulated with the anti-CD3 antibody/anti-CD28 antibody coated plate.

Day 4: The cells are transferred to G-Rex10, and cultured with TexMACS™ containing 10 ng/mL of IL-7 and 5 ng/mL of IL15.

Day 7: Half the amount of the culture solution is replaced with TexMACS™ containing 10 ng/mL of IL-7 and 5 ng/mL of IL15.

Day 10: Half the amount of the culture solution is replaced with TexMACS™ containing 10 ng/mL of IL-7 and 5 ng/mL of IL15.

Day 14: Culturing is finished.

Figure 2:
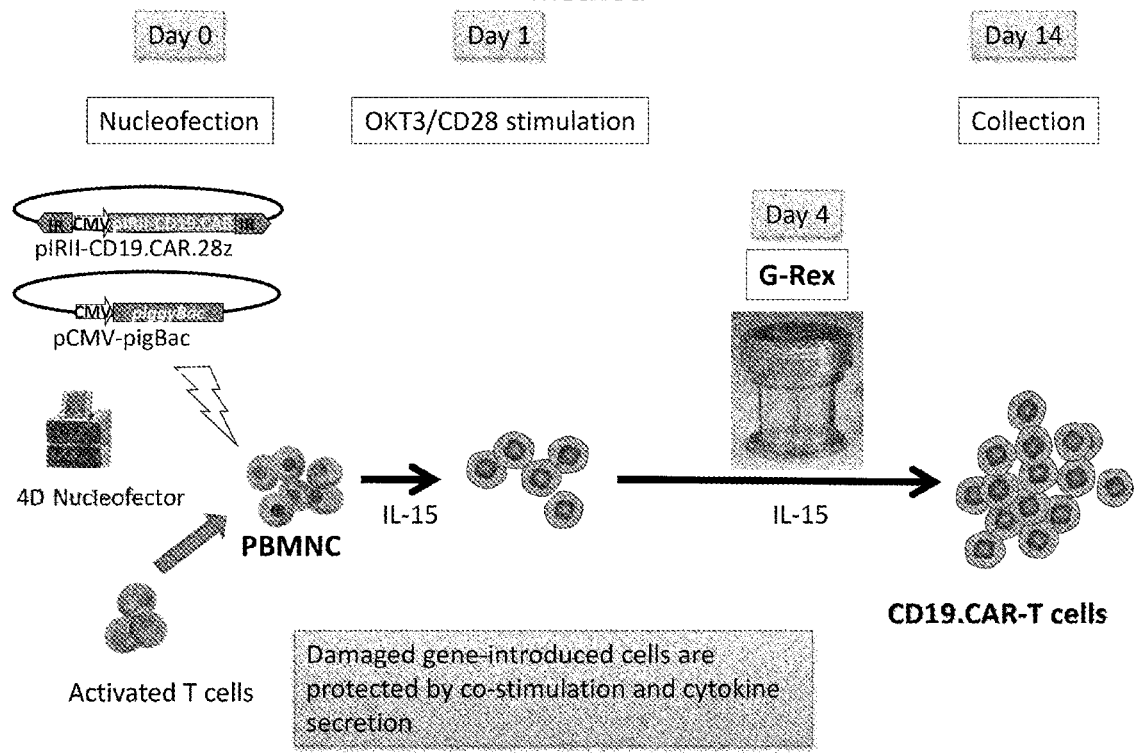
FIG. 2 depicts preparation and culturing of CAR-T cells by a novel method (culturing method 2).

(3) Preparation and Culturing of CAR-T by Activated T Cells Addition Method (See Culturing Method 2 and FIG. 2)

Day 0: Mononuclear cells are isolated from the peripheral blood. To $1 \times 10^7$ mononuclear cells, pIRII-CAR.CD19.28z vector (FIG. 4) and pCMV-pigBac vector (FIG. 5) are added in amounts of 5 μg, and the gene is introduced by electroporation (nucleofection). The gene-introduced cells and $5 \times 10^5$ irradiated activated T cells are mixed, the mixture is floated in TexMACS™ containing 10 ng/mL of IL-7 and 5 ng/mL of IL15, and culturing is started on a 24-well plate in an incubator at 37° C.

Day 1: The cells are stimulated with the anti-CD3 antibody/anti-CD28 antibody coated plate.

Day 4: The cells are transferred to G-Rex10, and cultured with TexMACS™ containing 10 ng/mL of IL-7 and 5 ng/mL of IL15.

Day 7: Half the amount of the culture solution is replaced with TexMACS™ containing 10 ng/mL of IL-7 and 5 ng/mL of IL15.

Day 10: Half the amount of the culture solution is replaced with TexMACS™ containing 10 ng/mL of IL-7 and 5 ng/mL of IL15.

Day 14: Culturing is finished.

Figure 3:
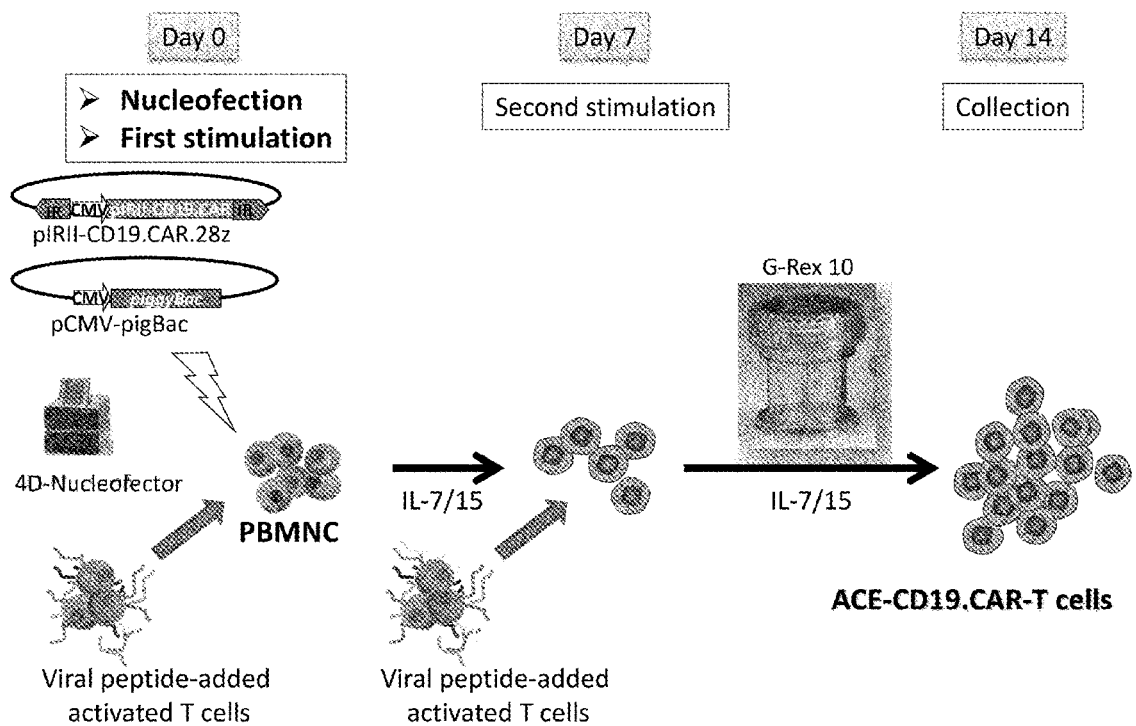
FIG. 3 depicts preparation and culturing of CAR-T cells by a novel method (culturing method 3).

(4) Preparation and Culturing of CAR-T by Viral Peptide-Added Activated T Cells Addition Method (See Culturing Method 3 and FIG. 3)

Day 0: $5 \times 10^5$ activated T cells after irradiation are mixed with the viral peptides (50 ng each of PepTivator CMV pp65, PepTivator AdV5 Hexon, PepTivator EBV EBNA-1, and PepTivator EBV BZLF1), and incubated at 37° C. for 30 minutes. To $1 \times 10^7$ mononuclear cells, pIRII-CAR.CD19.28z vector (FIG. 4) and pCMV-pigBac vector (FIG. 5) are added in amounts of 5 μg, and the gene is introduced by electroporation (nucleofection). The gene-introduced cells and the irradiated viral peptide-added activated T cells are mixed, the mixture is floated in TexMACS™ containing 10 ng/mL of IL-7 and 5 ng/mL of IL15, and culturing is started on a 24-well plate in an incubator at 37° C.

Day 2 to Day 5: As necessary, half the amount of the culture solution is replaced with TexMACS™ containing 10 ng/mL of IL-7 and 5 ng/mL of IL15.

Day 7: The cells are collected and counted. $2 \times 10^6$ viral peptide-added activated T cells papered in the same manner as described above and the collected cells are floated in 30 mL of a culture solution containing IL-15 (5 ng/mL) and IL-7 (10 ng/mL), and culturing is started with G-Rex10.

Day 10: Half the amount of the culture solution is replaced with TexMACS™ containing 10 ng/mL of IL-7 and 5 ng/mL of IL15.

Day 14: Culturing is finished.

3. Result

After completion of culturing (Day 14), the number of proliferated cells, the number of CAR-T cells, and the gene introduction efficiency (CAR-T cells/all living cells) were determined for each culturing method, and the results were compared between culturing methods 1 to 3. Measuring of the number of proliferated cells used a hemocytometer, and the number of CAR-T cells and the gene introduction efficiency were calculated from the result of flow cytometry analysis.

Figure 6:
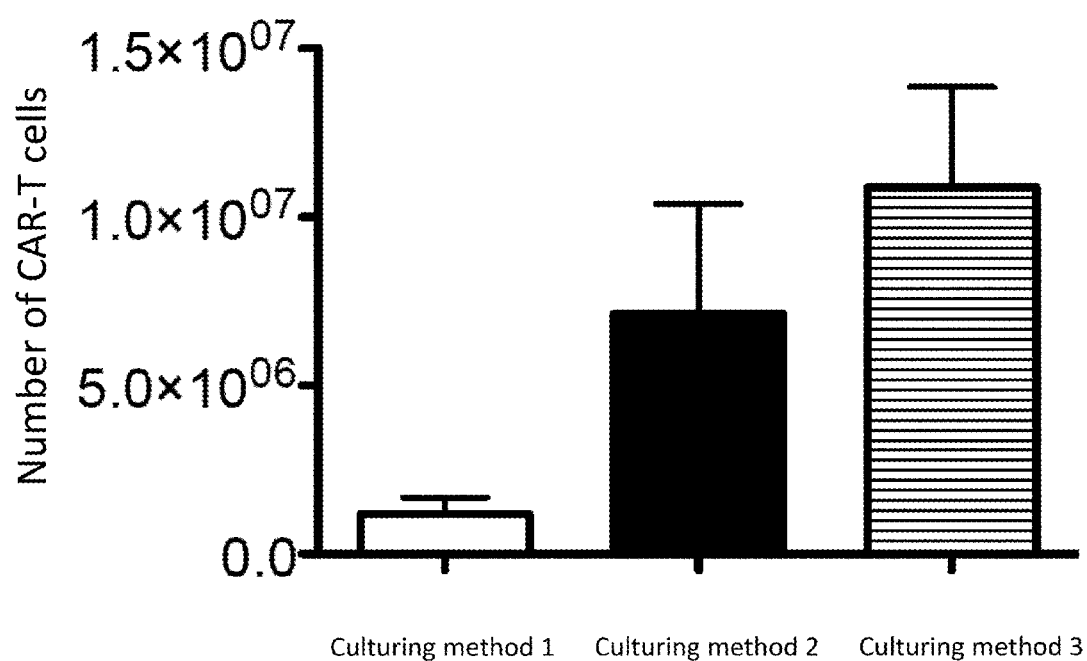
FIG. 6 depicts the number of the CAR-T cells obtained by each culturing method (average±standard error).
Figure 7:
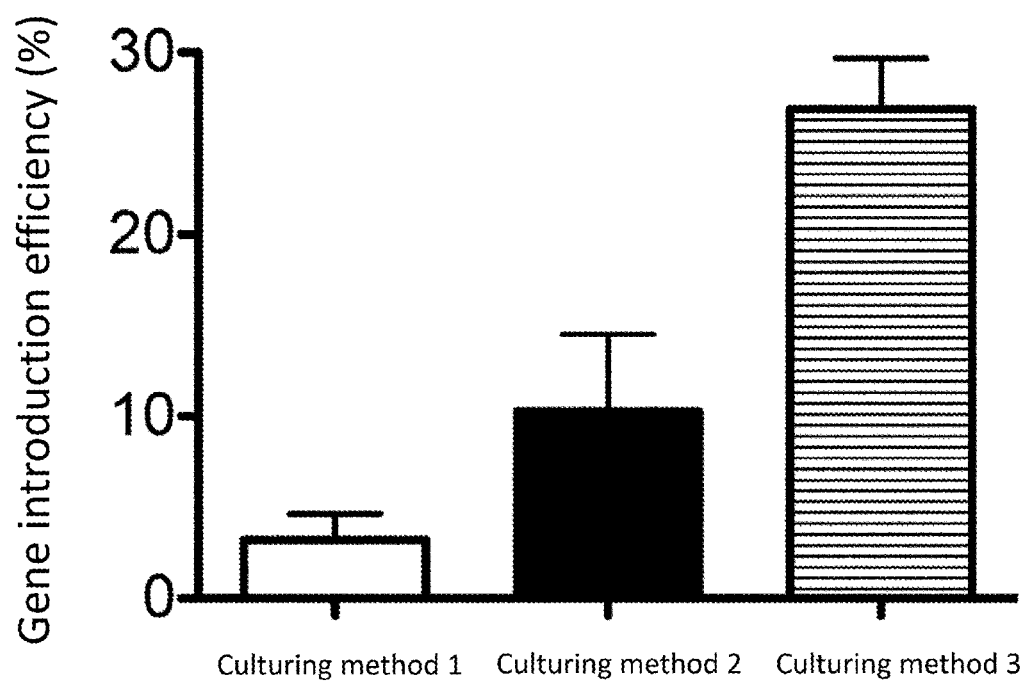
FIG. 7 depicts the gene introduction rate by each culturing method (average±standard error).

The number of CAR-T cells were $1.18 \times 10^6$ ($\pm 0.509 \times 10^6$) in culturing method 1, $7.13 \times 10^6$ ($\pm 3.25 \times 10^6$) in culturing method 2, and $1.09 \times 10^7$ ($\pm 2.98 \times 10^6$) in culturing method 3 (FIG. 6). The gene introduction efficiency was 3.22% ($\pm 1.42$) in culturing method 1, 10.3% ($\pm 4.21$) in culturing method 2, and 26.9% ($\pm 2.79$) in culturing method 3 (FIG. 7). The values in the parentheses are standard errors.

Figure 8:
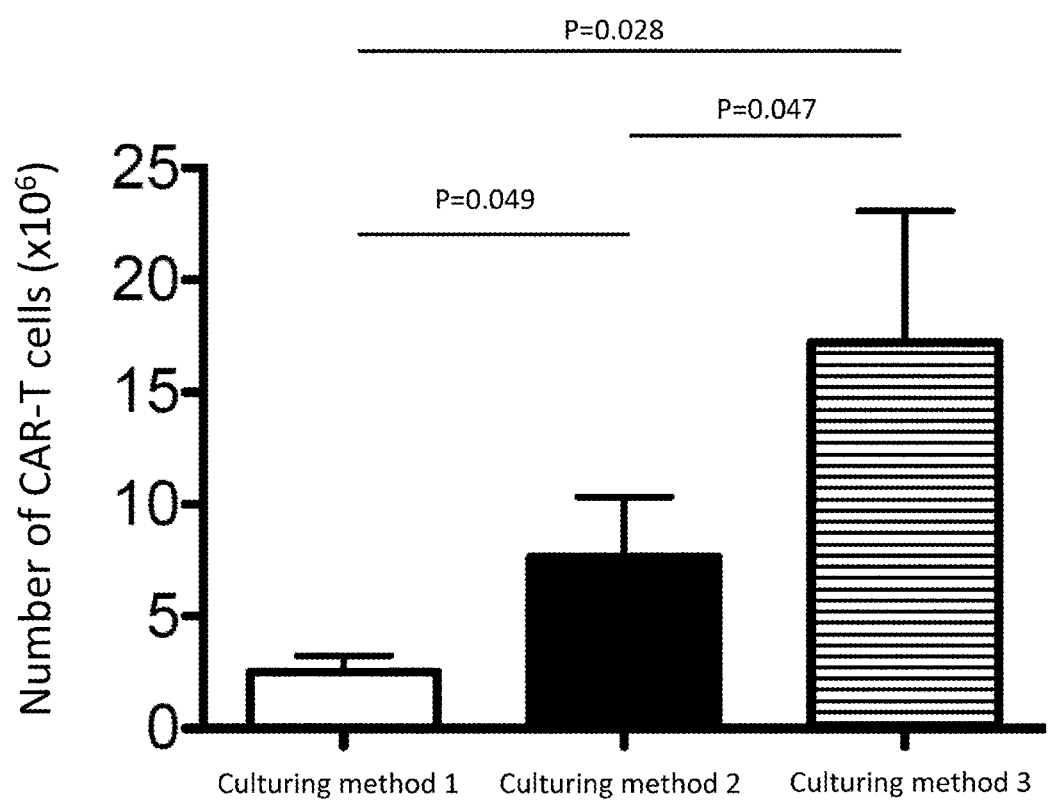
FIG. 8 depicts the number of the CAR-T cells obtained by each culturing method (average±standard error). N=9. Significant differences are found between the novel methods (culturing methods 2 and 3) and the prior art method (culturing method 1). Additionally, culturing method 3 brought a significantly higher number of CAR-T cells than culturing method 2.
Figure 9:
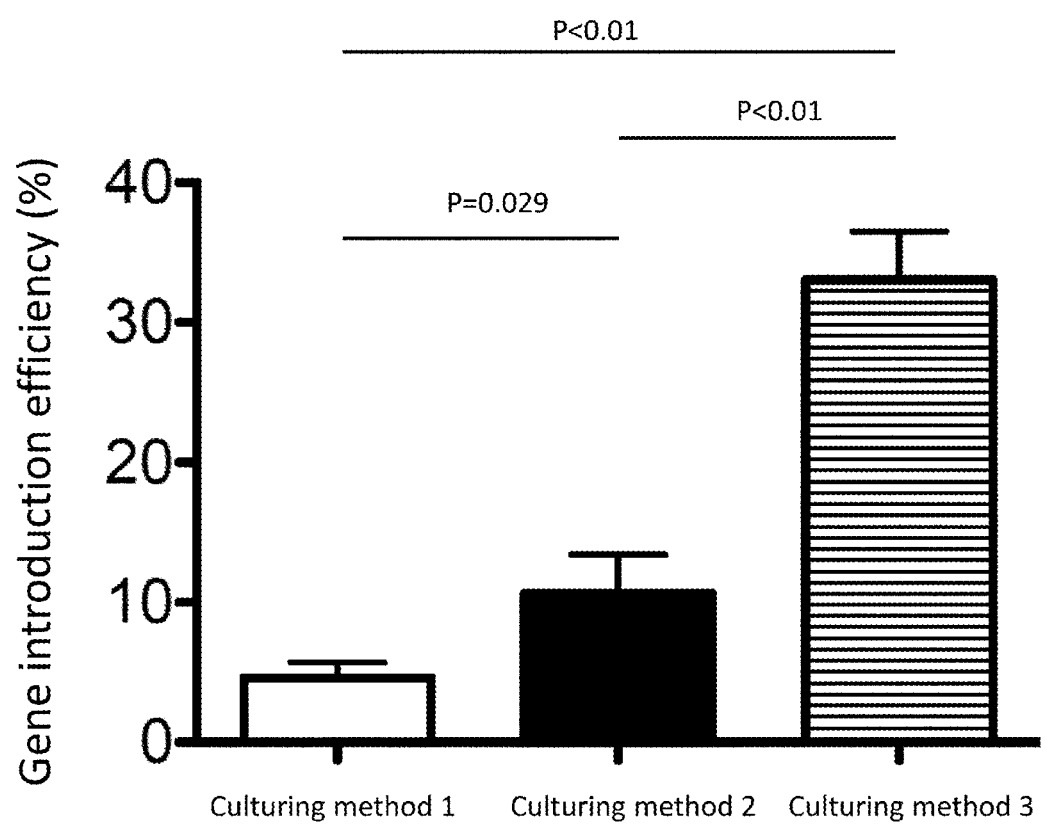
FIG. 9 depicts the gene introduction rate by each culturing method (average±standard error). N=9. Significant differences are found between the novel methods (culturing methods 2 and 3) and the prior art method (culturing method 1). Additionally, culturing method 3 had a significantly higher gene introduction rate than culturing method 2.

The number of the donors of the peripheral blood used for the preparation of CAR-T cells (N=9) was increased, and further studied. As a result of this, the number of CAR-T cells was $2.5 \times 10^6$ ($\pm 0.72 \times 10^6$) in culturing method 1, $7.6 \times 10^6$ ($\pm 2.6 \times 10^6$) in culturing method 2, and $17.2 \times 10^6$ ($\pm 5.8 \times 10^6$) in culturing method 3 (FIG. 8). The gene introduction efficiency was 4.6% ($\pm 1.1$) in culturing method 1, 10.7% ($\pm 2.7$) in culturing method 2, and 33.0% ($\pm 3.4$) in culturing method 3 (FIG. 9). The values in the parentheses are standard errors.

Figure 10:
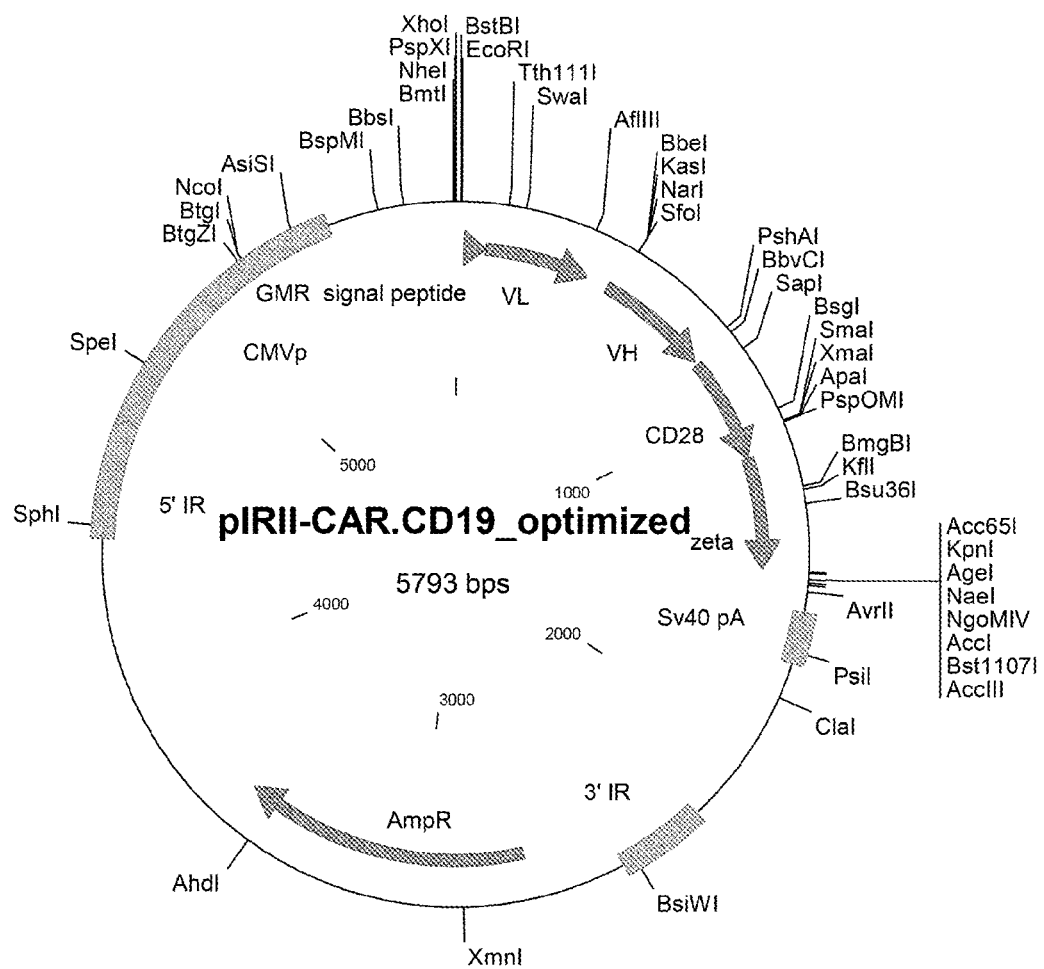
FIG. 10 depicts the structure of the pIRII-CAR.CD19_optimized vector (SEQ ID NO. 9), which is an optimized vector for CAR gene introduction. In comparison with the structure of the pIRII-CAR.CD19.28z vector, the Fc regions (CH2 and CH3) are deleted.
Figure 11:
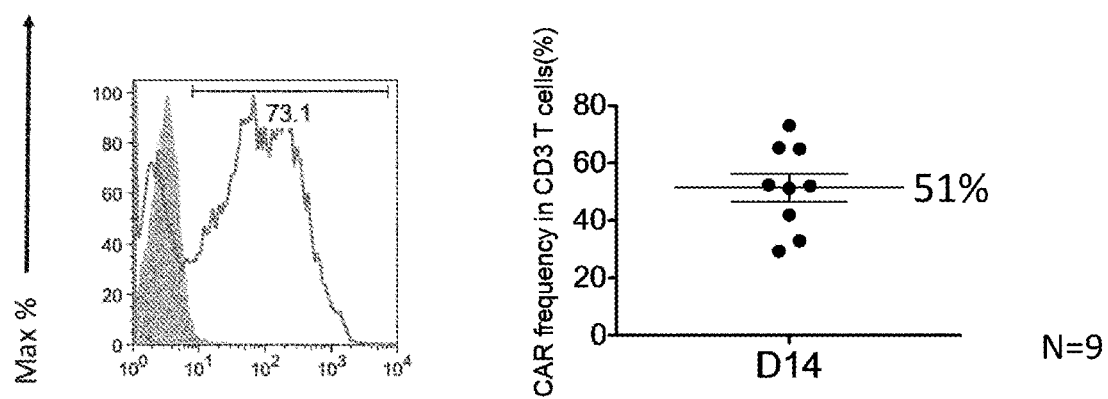
FIG. 11 depicts the gene introduction rate when the pIRII-CAR.CD19_optimized vector was used. The result of flow cytometry (left) and the proportion of the CAR expression cell in the CD3-positive T cells (right) are represented. N=9.

On the other hand, as a result of optimization of the plasmid (FIG. 10), in culturing method 3, the gene introduction efficiency of about 50% on average was achieved (FIG. 11).

As described above, in the novel culturing methods (culturing methods 2 and 3), in comparison with the prior art method (culturing method 1), the number of the CAR-T cells increased, and the gene introduction efficiency also increased. In culturing method 2, the increase of the number of CAR-T cells and the enhancement of the gene introduction efficiency were likely caused by the cell stimulation by the expression of costimulatory molecules (protective action on gene-introduced cells damaged during electroporation), cytokine stimulation by culturing micro-environment, and others. In culturing method 3, the increase of the number of CAR-T cells and the enhancement of the gene introduction efficiency were likely caused by the cell stimulation by the expression of costimulatory molecules, cytokine stimulation by culturing micro-environment, relatively moderate cell stimulation from the virus-specific T cells receptor, and others.

It has been found that the novel two culturing methods, more specifically, the novel culturing method (culturing method 2) using activated T cells and the novel culturing method (culturing method 3) using viral peptide-added activated T cells can solve the problems with CAR therapy using a transposon method. It is expected that the use of these culturing methods will further promote and expand the clinical application of CAR therapy. Culturing method 3 may cause the decrease of alloreactivity (the anticipated effect of virus-specific CTL), which can allow the possibility of the use of the CAR-T cells derived from the third party, and increase the internal persistency due to stimulation of the viral antigen receptor by internal viruses, and thus is expected to further promote safety and enhance the therapeutic effect.

<Improvement of Culturing Method 3>

1. Method

Day 0: Mononuclear cells (PBMCs) are isolated from the peripheral blood. A portion ($1 \times 10^6$ PBMCs) is irradiated, mixed with the viral peptides (50 ng each of PepTivator CMV pp65, PepTivator AdV5 Hexon, PepTivator EBV EBNA-1, and PepTivator EBV BZLF1), and incubated at 37° C. for 30 minutes. To $1 \times 10^7$ PBMCs, pIRII-CAR.CD19-optimized vector (FIG. 10) and pCMV-pigBac vector (FIG. 5) are added in amounts of 5 μg, and the gene is introduced by electroporation (nucleofection). The gene-introduced cells and the irradiated viral peptide-added PBMCs are mixed, the mixture is floated on TexMACS™ containing 10 ng/mL of IL-7 and 5 ng/mL of IL15, and culturing is started on a 24-well plate in an incubator at 37° C. The activated T cells are prepared from the remaining PBMCs according to the above-described method (1).

Day 2 to Day 5: As necessary, half the amount of the culture solution is replaced with TexMACS™ containing 10 ng/mL of IL-7 and 5 ng/mL of IL15.

Day 7: The cells are collected and counted. On the other hand, $2 \times 10^6$ activated T cells prepared by the above-described method are irradiated, and then the viral peptides (each 50 ng of PepTivator CMV pp65, PepTivator AdV5 Hexon, PepTivator EBV EBNA-1, and PepTivator EBV BZLF1) are added, and incubated at 37° C. for 30 minutes. The $2 \times 10^6$ viral peptide-added activated T cells thus obtained and the collected cells are floated in 30 mL of a culture solution containing IL-15 (5 ng/mL) and IL-7 (10 ng/mL), and culturing is started with G-Rex10.

Day 10: Half the amount of the culture solution is replaced with TexMACS™ containing 10 ng/mL of IL-7 and 5 ng/mL of IL15.

Day 14: Culturing is finished.

2. Result

After completion of culturing (day 14), the number of CAR-T cells and the gene introduction efficiency (CAR-T cells/all living cells) were determined. The number of CAR-T cells and the gene introduction efficiency were $2.81 \times 10^7$ and 55.1% in the first experiment, $1.03 \times 10^7$ and 52.0% in the second experiment, and $9.22 \times 10^6$ and 42.3% in the third experiment. These high gene introduction efficiencies were achieved. This culturing method allows obtainment of CAR-T cells by one time of blood collection, and has an advantage that the burden on patients is reduced.

<Evaluation of Activity of CAR-T Cells>

The cytotoxic activity and antitumor activity of the CAR-T cells prepared by the novel culturing method were evaluated by the following methods.

1. Experiment of Co-Culturing with CD19-Positive Leukemia Cell Line

CAR-T cells were prepared from the peripheral blood of six normal subjects using culturing method 3. CAR-T cells ($1 \times 10^5$) and a CD19-positive leukemia cell line ($5 \times 10^5$) were co-cultured for seven days in the 10% fetal bovine serum-containing RPMI1640 culture medium (effector cell: target cell=1:5). The control used the activated T cells without gene introduction (T cells prepared by culturing method 3, except for the gene introduction operation) in place of CAR-T cells. The cells were collected after co-culturing for seven days, stained with an anti-CD19 antibody and an anti-CD3 antibody, and then the number of cells was counted by counting beads and a flowcytometer. The number of residual tumor cells was calculated by the following calculation formula, and the cytotoxic activity of the CAR-T cells was evaluated. The above experiment was carried out using three kinds of CD19-positive leukemia cell lines (KOPN30bi, SK-9, and TCC-Y/sr).

Figure 12:
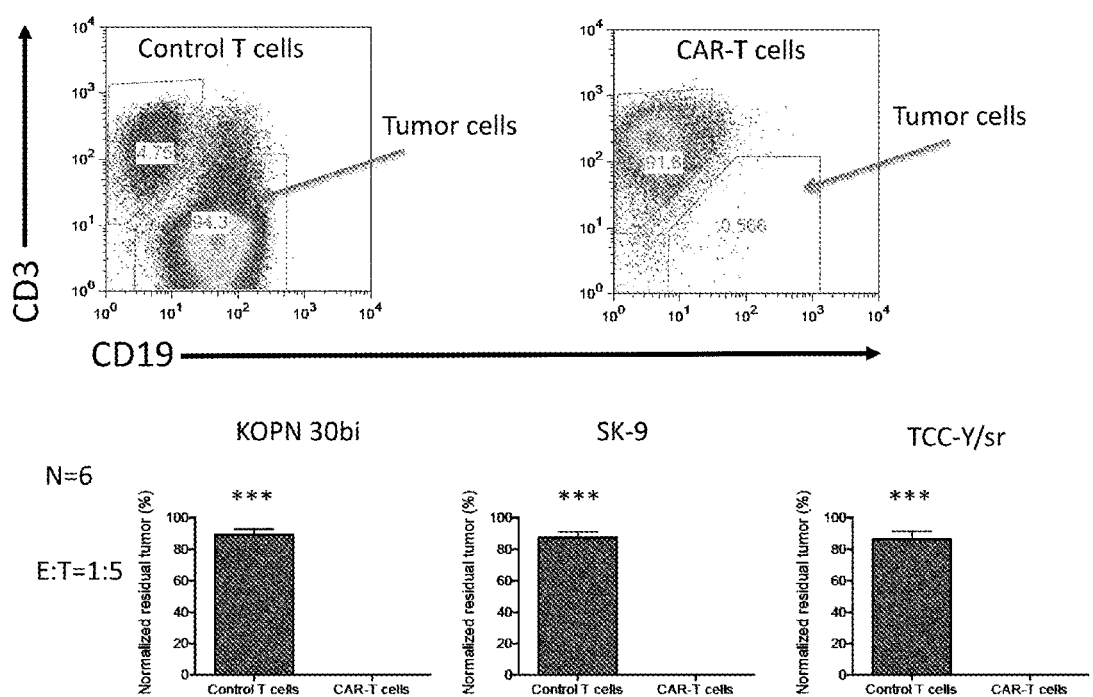
FIG. 12 depicts the result of cytotoxic activity test. The results of flow cytometry (top) and tumor cell residual rate (bottom) are given. Three kinds of CD19-positive leukemia cell lines (KOPN30bi, SK-9, and TCC-Y/sr) and CAR-T cells were co-cultured, and the cytotoxic activity was evaluated. N=6.

Standardized tumor cell residual rate (%)=100×(the number of residual tumor cells in the well co-cultured with T cells–the number of tumor cells in the well not co-cultured with T cells)/the number of tumor cells in the well not co-cultured with T cells The result is given in FIG. 12. When co-cultured with CAR-T cells, the residual rate of KOPN30bi was 0.2% (the control was 89%), the residual rate of SK-9 was 0.03% (the control was 87%), and TCC-Y/sr was 0.03% (the control was 86%), indicating that the CAR-T cells had strong cytotoxic activity.

2. Evaluation by Tumor-Bearing Mouse

The CAR-T cells ($1 \times 10^7$) prepared by culturing method 3 were injected into the NSG mice (five animals in each test section), to which the CD19-positive cell strain (luciferase gene-introduced Daudi, $1 \times 10^6$) had been injected three days before (D-3) from their tail vein, from their tail vein (D0). In the control (NT), activated T cells with no introduced gene (the T cells prepared by culturing method 3 except for the gene introduction operation) were injected. As necessary, luciferin was intraperitoneally administered, and the mouse was photographed using an in vivo imaging system.

Figure 13:
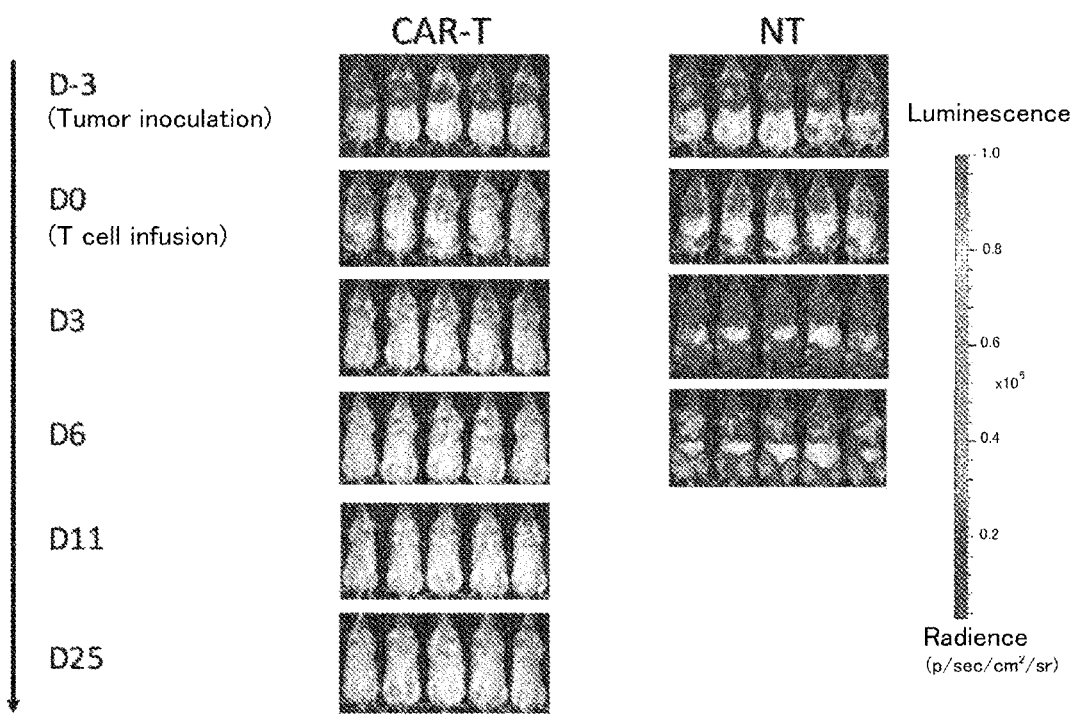
FIG. 13 depicts the result of antitumor activity test. After administering CAR-T cells to tumor-bearing mice, the proliferation of tumor cells was monitored with an in vivo imaging system.

As given in FIG. 13, proliferation of the tumor cells was not observed in the mice treated with the proliferated CAR-T cells, in contrast to the mice treated with the activated T cells with no gene introduction (control (NT)) in which the tumor cells proliferated. More specifically, the CAR-T cells strongly suppressed proliferation of tumor in the tumor-bearing mice.

3. Summary

As described above, it was confirmed that the CAR-T cells prepared by the novel culturing method exhibits high activity by the in vitro and in vivo experiments. More specifically, it was indicated that the novel culturing method is highly effective as a means for efficiently preparing CAR-T cells having high therapeutic effect.

INDUSTRIAL APPLICABILITY

The present invention increases the CAR gene introduction efficiency and the cell proliferation rate in the preparation of CAR-T cells using a transposon method. More specifically, the present invention increases practicability of the highly safe method for preparing CAR-T cells using a transposon method, thereby promoting clinical application of CAR therapy, and contributing to the increase of the therapeutic effect of CAR therapy.

The present invention is not limited only to the description of the above embodiments. A variety of modifications which are within the scopes of the following claims and which are achieved easily by a person skilled in the art are included in the present invention.

The invention claimed is:

1. A method for preparing genetically-modified T cells expressing chimeric antigen receptor, comprising the following steps (1) to (4):
   (1) a step of preparing non-proliferative cells which are obtained by stimulating a group of cells comprising T cells using an anti-CD3 antibody and an anti-CD28 antibody followed by a treatment for causing the cells to lose their proliferation capability;
   (2) a step of introducing a target antigen-specific chimeric antigen receptor gene into T cells using a transposon method and thereby obtaining the genetically-modified T cells;
   (3) a step of mixing the non-proliferative cells prepared by step (1) with the genetically-modified T cells obtained by step (2), and co-culturing the mixed cells while stimulating the mixed cells using an anti-CD3 antibody and anti-CD28 antibody; and
   (4) a step of collecting the cells after culture;
   wherein the step (1) is conducted in advance of step (2);
   wherein introducing the target antigen-specific chimeric antigen receptor gene into the T cells and mixing the genetically-modified T cells with the non-proliferative cells are conducted on the same day.

2. The preparation method according to claim 1, wherein, after the cells are co-cultured, a step of culturing the co-cultured cells in the presence of a T-cell growth factor is carried out between step (3) and step (4).

3. The preparation method according to claim 1, wherein the period of the co-culturing in step (3) is one day to 14 days.

4. The preparation method according to claim 1, wherein step (3) is carried out in the presence of a T-cell growth factor.

5. The preparation method according to claim 4, wherein the T-cell growth factor is IL-15.

6. The preparation method according to claim 4, wherein the T-cell growth factor is a combination of IL-15 and IL-7.

7. The preparation method according to claim 1, wherein the group of cells comprising T cells is peripheral blood mononuclear cells (PBMCs).

8. The preparation method according to claim 1, wherein the treatment for losing the proliferation capability is irradiation.

9. The preparation method according to claim 1, wherein the transposon method comprises preparing a vector including the gene coding transposase and a vector having a structure wherein the gene coding a target protein is sandwiched between inverted repeat sequences, and introducing these vectors to the target cell.

10. The preparation method according to claim 1, wherein the target antigen is the CD19, GD2, GMCSF receptor or the IGF receptor.

11. The preparation method according to claim 1, wherein the non-proliferative cells and the genetically-modified T cells are derived from an identical individual.

* * * * *

SEQUENCE LISTING

```
<160> NUMBER OF SEQ ID NOS: 9

<210> SEQ ID NO 1
<211> LENGTH: 6438
<212> TYPE: DNA
<213> ORGANISM: Artificial Sequence
<220> FEATURE:
<223> OTHER INFORMATION: pIRII-CAR.CD19.28z
<220> FEATURE:
<221> NAME/KEY: misc_feature
<222> LOCATION: (30)..(86)
<223> OTHER INFORMATION: Leader
<220> FEATURE:
<221> NAME/KEY: misc_feature
<222> LOCATION: (87)..(416)
<223> OTHER INFORMATION: VL
<220> FEATURE:
<221> NAME/KEY: misc_feature
<222> LOCATION: (486)..(833)
```

```
<223> OTHER INFORMATION: VH
<220> FEATURE:
<221> NAME/KEY: misc_feature
<222> LOCATION: (867)..(1562)
<223> OTHER INFORMATION: CH2CH3
<220> FEATURE:
<221> NAME/KEY: misc_feature
<222> LOCATION: (1575)..(1778)
<223> OTHER INFORMATION: CD28
<220> FEATURE:
<221> NAME/KEY: misc_feature
<222> LOCATION: (1779)..(2117)
<223> OTHER INFORMATION: CD3 zeta
<220> FEATURE:
<221> NAME/KEY: misc_feature
<222> LOCATION: (2850)..(3085)
<223> OTHER INFORMATION: 3' IR
<220> FEATURE:
<221> NAME/KEY: misc_feature
<222> LOCATION: (5031)..(5341)
<223> OTHER INFORMATION: 5' IR

<400> SEQUENCE: 1
tcgagctcaa gcttcgaatt cgaatggcca tggagtttgg gctgagctgg cttttcttg        60 tggctatttt aaaaggtgtc cagtgctcta gagacatcca gatgacacag actacatcct      120
ccctgtctgc ctctctggga gacagagtca ccatcagttg cagggcaagt caggacatta      180
gtaaatattt aaattggtat cagcaaaaac cagatggaac tgttaaactc ctgatctacc      240
atacatcaag attacactca ggagtcccat caaggttcag tggcagtggg tctggaacag      300
attattctct caccattagc aacctggagc aagaagatat tgccacttac ttttgccaac      360
agggtaatac gcttccgtac acgttcgagg ggggaccaa gctggagctg aaacgtggtg       420
gtggtggttc tggtggtggt ggttctggcg gcggcggctc cggtggtggt ggatccgagg      480
tgcagctgca gcagtctgga cctggcctgg tggcgccctc acagagcctg tccgtcacat      540
gcactgtctc agggtctca ttacccgact atggtgtaag ctggattcgc agcctccac        600 gaaagggtct ggagtggctg ggagtaatat ggggtagtga aaccacatac tataattcag      660
ctctcaaatc cagactgacc atcatcaagg acaactccaa gagccaagtt tccttaaaaa      720
tgaacagtct gcaaactgat gacacagcca tttactactg tgccaaacat tattactacg      780
gtggtagcta tgctatggac tactggggcc aagggaccac ggtcaccgtc tcctcgtacg      840
tcaccgtctc ttcacaggat cccgccgagc ccaaatctcc tgacaaaact cacacatgcc      900
caccgtgccc agcacctgaa ctcctggggg gaccgtcagt cttcctcttc cccccaaaac      960
ccaaggacac cctcatgatc tcccggaccc ctgaggtcac atgcgtggtg gtggacgtga     1020
gccacgaaga ccctgaggtc aagttcaact ggtacgtgga cggcgtggag gtgcataatg     1080
ccaagacaaa gccgcgggag gagcagtaca acagcacgta ccgtgtggtc agcgtcctca     1140
ccgtcctgca ccaggactgg ctgaatggca aggagtacaa gtgcaaggtc tccaacaaag     1200
ccctcccagc ccccatcgag aaaaccatct ccaaagccaa aggcagcccc gagaaccac      1260 aggtgtacac cctgccccca tcccgggatg agctgaccaa gaaccaggtc agcctgacct     1320
gcctggtcaa aggcttctat cccagcgaca tcgccgtgga gtgggagagc aatgggcaac     1380
cggagaacaa ctacaagacc acgcctcccg tgctggactc cgacggctcc ttcttcctct     1440
acagcaagct caccgtggac aagagcaggt ggcagcaggg gaacgtcttc tcatgctccg     1500
tgatgcatga ggctctgcac aaccactaca cgcagaagag cctctccctg tctccgggta     1560
aaaaagatcc caaattttgg gtgctggtgg tggttggtgg agtcctggct tgctatagct     1620
tgctagtaac agtggccttt attatttct gggtgaggag taagaggagc aggctcctgc      1680
```

```
acagtgacta catgaacatg actccccgcc gccccgggcc cacccgcaag cattaccagc    1740
cctatgcccc accacgcgac ttcgcagcct atcgctccag agtgaagttc agcaggagcg    1800
cagacgcccc cgcgtaccag cagggccaga accagctcta taacgagctc aatctaggac    1860
gaagagagga gtacgatgtt ttggacaaga gacgtggccg ggaccctgag atgggggaa    1920 agccgagaag gaagaaccct caggaaggcc tgtacaatga actgcagaaa gataagatgg    1980
cggaggccta cagtgagatt gggatgaaag gcgagcgccg gaggggcaag gggcacgatg    2040
gcctttacca gggtctcagt acagccacca aggacaccta cgacgcccett cacatgcagg    2100 ccctgcctcc tcgctaagca tgctagctat agttctagag gtaccggttg ttaacgttag    2160
ccggctacgt atactccgga atattaatag gcctaggatg catatggcgg ccgcttccct    2220
ttagtgaggg ttaatgcttc gagcagacat gataagatac attgatgagt ttggacaaac    2280
cacaactaga atgcagtgaa aaaaatgctt tatttgtgaa atttgtgatg ctattgcttt    2340
atttgtaacc attataagct gcaataaaca agttaacaac aacaattgca ttcattttat    2400
gtttcaggtt caggggggaga tgtgggaggt ttttttaaagc aagtaaaacc tctacaaatg    2460
tggtaaaatc cgataaggat cgatccgggc tggcgtaata gcgaagaggc ccgcaccgat    2520
cgcccttccc aacagttgcg cagcctgaat ggcgaatgga cgcgccctgt agcggcgcat    2580
taagcgcggc gggtgtggtg gttacgcgca gcgtgaccgc tacacttgcc agcgccctag    2640
cgcccgctcc tttcgctttc ttcccttcct ttctcgccac gttcgcccga tagcgataag    2700
gatccgcgta tggtgcactc tcagtacaat ctgctctgat gccgcatagt taagccagcc    2760
ccgacacccg ccaacacccg ctgacgcgcc ctgacgggct tgtctgctcc cggcatccgc    2820
ttacagacaa gctgtgaccg tctccgggat tttgttactt tatagaagaa attttgagtt    2880
tttgtttttt tttaataaat aaataaacat aaataaattg tttgttgaat ttattattag    2940
tatgtaagtg taaatataat aaaacttaat atctattcaa attaataaat aaacctcgat    3000
atacagaccg ataaaacaca tgcgtcaatt ttacgcatga ttatctttaa cgtacgtcac    3060
aatatgatta tctttctagg gttaatccgg gagctgcatg tgtcagaggt tttcaccgtc    3120
atcaccgaaa cgcgcgagac gaaagggcct cgtgatacgc ctatttttat aggttaatgt    3180
catgataata atggtttctt agacgtcagg tggcacttttt cggggaaatg tgcgcggaac    3240
ccctatttgt ttattttttct aaatacattc aaatatgtat ccgctcatga gacaataacc    3300
ctgataaatg cttcaataat attgaaaaag gaagagtatg agtattcaac atttccgtgt    3360
cgcccttatt ccctttttttg cggcattttg ccttcctgtt tttgctcacc cagaaacgct    3420
ggtgaaagta aaagatgctg aagatcagtt gggtgcacga gtgggttaca tcgaactgga    3480
tctcaacagc ggtaagatcc ttgagagttt tcgccccgaa gaacgttttc caatgatgag    3540
cacttttaaa gttctgctat gtggcgcggt attatcccgt attgacgccg ggcaagagca    3600
actcggtcgc cgcatacact attctcagaa tgacttggtt gagtactcac cagtcacaga    3660
aaagcatctt acggatggca tgacagtaag agaattatgc agtgctgcca taaccatgag    3720
tgataacact gcggccaact tacttctgac aacgatcgga ggaccgaagg agctaaccgc    3780
ttttttgcac aacatggggg atcatgtaac tcgccttgat cgttgggaac cggagctgaa    3840
tgaagccata ccaaacgacg agcgtgacac cacgatgcct gtagcaatgg caacaacgtt    3900
gcgcaaacta ttaactggcg aactacttac tctagcttcc cggcaacaat taatagactg    3960
gatggaggcg gataaagttg caggaccact tctgcgctcg gcccttccgg ctggctggtt    4020
```

```
tattgctgat aaatctggag ccggtgagcg tgggtctcgc ggtatcattg cagcactggg      4080
gccagatggt aagccctccc gtatcgtagt tatctacacg acggggagtc aggcaactat      4140
ggatgaacga aatagacaga tcgctgagat aggtgcctca ctgattaagc attggtaact      4200
gtcagaccaa gtttactcat atatacttta gattgattta aaacttcatt tttaatttaa      4260
aaggatctag gtgaagatcc tttttgataa tctcatgacc aaaatccctt aacgtgagtt      4320
ttcgttccac tgagcgtcag accccgtaga aaagatcaaa ggatcttctt gagatccttt      4380
ttttctgcgc gtaatctgct gcttgcaaac aaaaaaacca ccgctaccag cggtggtttg      4440
tttgccggat caagagctac caactctttt tccgaaggta actggcttca gcagagcgca      4500
gataccaaat actgttcttc tagtgtagcc gtagttaggc caccacttca agaactctgt      4560
agcaccgcct acatacctcg ctctgctaat cctgttacca gtggctgctg ccagtggcga      4620
taagtcgtgt cttaccgggt tggactcaag acgatagtta ccggataagg cgcagcggtc      4680
gggctgaacg gggggttcgt gcacacagcc cagcttggag cgaacgacct acaccgaact      4740 gagatacccta cagcgtgagc tatgagaaag cgccacgctt cccgaaggga gaaaggcgga      4800
caggtatccg gtaagcggca gggtcggaac aggagagcgc acgagggagc ttccaggggg      4860
aaacgcctgg tatctttata gtcctgtcgg gtttcgccac ctctgacttg agcgtcgatt      4920
tttgtgatgc tcgtcagggg ggcggagcct atggaaaaac gccagcaacg cggccttttt      4980
acggttcctg gccttttgct ggccttttgc tcacatggct cgacagatct ttaaccctag      5040
aaagatagtc tgcgtaaaat tgacgcatgc attcttgaaa tattgctctc tctttctaaa      5100
tagcgcgaat ccgtcgctgt gcatttagga catctcagtc gccgcttgga gctcccgtga      5160
ggcgtgcttg tcaatgcggt aagtgtcact gattttgaac tataacgacc gcgtgagtca      5220
aaatgacgca tgattatctt ttacgtgact tttaagattt aactcatacg ataattatat      5280
tgttatttca tgttctactt acgtgataac ttattatata tatattttct tgttatagat      5340
aagatcttca atattggcca ttagccatat tattcattgg ttatatagca taaatcaata      5400
ttggctattg gccattgcat acgttgtatc tatatcataa tatgtacatt tatattggct      5460
catgtccaat atgaccgcca tgttggcatt gattattgac tagttattaa tagtaatcaa      5520
ttacggggtc attagttcat agcccatata tggagttccg cgttacataa cttacggtaa      5580
atggcccgcc tggctgaccg cccaacgacc cccgcccatt gacgtcaata atgacgtatg      5640
ttcccatagt aacgccaata gggactttcc attgacgtca atgggtggag tatttacggt      5700
aaactgccca cttggcagta catcaagtgt atcatatgcc aagtccgccc cctattgacg      5760
tcaatgacgg taaatggccc gcctggcatt atgcccagta catgacctta cgggactttc      5820
ctacttggca gtacatctac gtattagtca tcgctattac catggtgatg cggttttggc      5880
agtacaccaa tgggcgtgga tagcggtttg actcacgggg atttccaagt ctccacccca      5940
ttgacgtcaa tgggagtttg ttttggcacc aaaatcaacg ggactttcca aaatgtcgta      6000
acaactgcga tcgcccgccc cgttgacgca aatgggcggt aggcgtgtac ggtgggaggt      6060
ctatataagc agagctcgtt tagtgaaccg tcagatcact agaagcttta ttgcggtagt      6120
ttatcacagt taaattgcta acgcagtcag tgcttctgac acaacagtct cgaacttaag      6180
ctgcagtgac tctcttaagg tagccttgca gaagttggtc gtgaggcact gggcaggtaa      6240
gtatcaaggt tacaagacag gtttaaggag accaatagaa actgggcttg tcgagacaga      6300
gaagactctt gcgtttctga taggcaccta ttggtcttac tgacatccac tttgcctttc      6360
tctccacagg tgtccactcc cagttcaatt acagctctta aggctagagt acttaatacg      6420
```
actcactata ggctagcc    6438

<210> SEQ ID NO 2
<211> LENGTH: 19
<212> TYPE: PRT
<213> ORGANISM: Artificial Sequence
<220> FEATURE:
<223> OTHER INFORMATION: Leader

<400> SEQUENCE: 2

Met Glu Phe Gly Leu Ser Trp Leu Phe Leu Val Ala Ile Leu Lys Gly
1               5                   10                  15

Val Gln Cys

<210> SEQ ID NO 3
<211> LENGTH: 110
<212> TYPE: PRT
<213> ORGANISM: Artificial Sequence
<220> FEATURE:
<223> OTHER INFORMATION: VL

<400> SEQUENCE: 3

Ser Arg Asp Ile Gln Met Thr Gln Thr Thr Ser Ser Leu Ser Ala Ser
1               5                   10                  15

Leu Gly Asp Arg Val Thr Ile Ser Cys Arg Ala Ser Gln Asp Ile Ser
                20                  25                  30

Lys Tyr Leu Asn Trp Tyr Gln Gln Lys Pro Asp Gly Thr Val Lys Leu
            35                  40                  45

Leu Ile Tyr His Thr Ser Arg Leu His Ser Gly Val Pro Ser Arg Phe
        50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Tyr Thr Phe Gly Gly Gly Thr Lys Leu Glu Leu Lys Arg
            100                 105                 110

<210> SEQ ID NO 4
<211> LENGTH: 116
<212> TYPE: PRT
<213> ORGANISM: Artificial Sequence
<220> FEATURE:
<223> OTHER INFORMATION: VH

<400> SEQUENCE: 4

Leu Gln Gln Ser Gly Pro Gly Leu Val Ala Pro Ser Gln Ser Leu Ser
1               5                   10                  15

Val Thr Cys Thr Val Ser Gly Val Ser Leu Pro Asp Tyr Gly Val Ser
                20                  25                  30

Trp Ile Arg Gln Pro Pro Arg Lys Gly Leu Glu Trp Leu Gly Val Ile
            35                  40                  45

Trp Gly Ser Glu Thr Thr Tyr Tyr Asn Ser Ala Leu Lys Ser Arg Leu
        50                  55                  60

Thr Ile Ile Lys Asp Asn Ser Lys Ser Gln Val Phe Leu Lys Met Asn
65                  70                  75                  80

Ser Leu Gln Thr Asp Asp Thr Ala Ile Tyr Tyr Cys Ala Lys His Tyr
                85                  90                  95

Tyr Tyr Gly Gly Ser Tyr Ala Met Asp Tyr Trp Gly Gln Gly Thr Thr
            100                 105                 110

```
Val Thr Val Ser
        115

<210> SEQ ID NO 5
<211> LENGTH: 232
<212> TYPE: PRT
<213> ORGANISM: Artificial Sequence
<220> FEATURE:
<223> OTHER INFORMATION: CH2CH3

<400> SEQUENCE: 5

Glu Pro Lys Ser Pro Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 68
<212> TYPE: PRT
<213> ORGANISM: Artificial Sequence
<220> FEATURE:
<223> OTHER INFORMATION: CD28

<400> SEQUENCE: 6

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
```

Ala Tyr Arg Ser
65

<210> SEQ ID NO 7
<211> LENGTH: 112
<212> TYPE: PRT
<213> ORGANISM: Artificial Sequence
<220> FEATURE:
<223> OTHER INFORMATION: CD3zeta

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 5413
<212> TYPE: DNA
<213> ORGANISM: Artificial Sequence
<220> FEATURE:
<223> OTHER INFORMATION: pCMV-pigBac
<220> FEATURE:
<221> NAME/KEY: misc_feature
<222> LOCATION: (826)..(2610)
<223> OTHER INFORMATION: piggyBac

<400> SEQUENCE: 8
gaattcgagc ttgcatgcct gcaggtcgtt acataactta cggtaaatgg cccgcctggc      60
tgaccgccca cgaccccccg cccattgacg tcaataatga cgtatgttcc catagtaacg     120
ccaataggga ctttccattg acgtcaatgg gtggagtatt tacggtaaac tgcccacttg     180
gcagtacatc aagtgtatca tatgccaagt acgcccccta ttgacgtcaa tgacggtaaa     240
tggcccgcct ggcattatgc ccagtacatg accttatggg actttcctac ttggcagtac     300
atctacgtat tagtcatcgc tattaccatg gtgatgcggt tttggcagta catcaatggg     360
cgtggatagc ggtttgactc acggggattt ccaagtctcc accccattga cgtcaatggg     420
agtttgtttt ggcaccaaaa tcaacgggac tttccaaaat gtcgtaacaa ctccgcccca     480
ttgacgcaaa tgggcggtag gcgtgtacgg tgggaggtct atataagcag agctcgttta     540
gtgaaccgtc agatcgcctg gagacgccat ccacgctgtt ttgacctcca tagaagacac     600
cgggaccgat ccagcctccg gactctagag gatccggtac tcgaggaact gaaaaaccag     660
aaagttaact ggtaagttta gtcttttttgt ctttatttc aggtcccgga tccggtggtg     720
gtgcaaatca agaactgct cctcagtgga tgttgccttt acttctaggc ctgtacggaa     780
gtgttacttc tgctctaaaa gctgcggaat tgtacccgcg gataaaatgg gtagttcttt     840
agacgatgag catatcctct ctgctcttct gcaaagcgat gacgagcttg ttggtgagga     900

```
ttctgacagt gaaatatcag atcacgtaag tgaagatgac gtccagagcg atacagaaga    960
agcgtttata gatgaggtac atgaagtgca gccaacgtca agcggtagtg aaatattaga   1020
cgaacaaaat gttattgaac aaccaggttc ttcattggct tctaacagaa tcttgacctt   1080
gccacagagg actattagag gtaagaataa acattgttgg tcaacttcaa agtccacgag   1140
gcgtagccga gtctctgcac tgaacattgt cagatctcaa agaggtccga cgcgtatgtg   1200
ccgcaatata tatgacccac ttttatgctt caaactattt tttactgatg agataatttc   1260
ggaaattgta aaatggacaa atgctgagat atcattgaaa cgtcgggaat ctatgacagg   1320
tgctacattt cgtgacacga atgaagatga aatctatgct ttctttggta ttctggtaat   1380
gacagcagtg agaaaagata accacatgtc cacagatgac ctctttgatc gatctttgtc   1440
aatggtgtac gtctctgtaa tgagtcgtga tcgttttgat tttttgatac gatgtcttag   1500
aatggatgac aaaagtatac ggcccacact tcgagaaaac gatgtattta ctcctgttag   1560
aaaaatatgg gatctcttta tccatcagtg catacaaaat tacactccag ggctcatttt   1620
gaccatagat gaacagttac ttggttttag aggacggtgt ccgtttagga tgtatatccc   1680
aaacaagcca gtaagtatg gaataaaaat cctcatgatg tgtgacagtg gtacgaagta   1740
tatgataaat ggaatgcctt atttgggaag aggaacacag accaacggag taccactcgg   1800
tgaatactac gtgaaggagt tatcaaagcc tgtgcacggt agttgtcgta atattacgtg   1860
tgacaattgg ttcacctcaa tccctttggc aaaaaactta ctacaagaac cgtataagtt   1920
aaccattgtg ggaaccgtgc gatcaaacaa acgcgagata ccggaagtac tgaaaaacag   1980
tcgctccagg ccagtgggaa catcgatgtt ttgttttgac ggaccccttta ctctcgtctc   2040
atataaaccg aagccagcta agatggtata cttattatca tcttgtgatg aggatgcttc   2100
tatcaacgaa agtaccggta aaccgcaaat ggttatgtat taatcaaa ctaaaggcgg    2160
agtggacacg ctagaccaaa tgtgttctgt gatgacctgc agtaggaaga cgaataggtg   2220
gcctatggca ttattgtacg gaatgataaa cattgcctgc ataaattctt ttattatata   2280
cagccataat gtcagtagca agggagaaaa ggttcaaagt cgcaaaaaat ttatgagaaa   2340
cctttacatg agcctgacgt catcgtttat gcgtaagcgt ttagaagctc ctactttgaa   2400
gagatatttg cgcgataata tctctaatat tttgccaaat gaagtgcctg gtacatcaga   2460
tgacagtact gaagagccag taatgaaaaa acgtacttac tgtacttact gcccctctaa   2520
aataaggcga aaggcaaatg catcgtgcaa aaaatgcaaa aaagttattt gtcgagagca   2580
taatattgat atgtgccaaa gttgtttctg actgactaat aagtataatt tgtttctatt   2640
atgtataagt taagctaatt aggatctaag ctgcaataaa caagttaaca acaacaattg   2700
cattcatttt atgtttcagg ttcagggga ggtgtgggag gttttttcgg atcctctaga   2760
gtcgacctgc aggcatgcaa gcttggcgta atcatggtca gctgtttc ctgtgtgaaa    2820
ttgttatccg ctcacaattc cacacaacat acgagccgga agcataaagt gtaaagcctg   2880
gggtgcctaa tgagtgagct aactcacatt aattgcgttg cgctcactgc ccgctttcca   2940
gtcgggaaac ctgtcgtgcc agctgcatta atgaatcggc caacgcgcgg ggagaggcgg   3000
tttgcgtatt gggcgctctt ccgcttcctc gctcactgac tcgctgcgct cggtcgttcg   3060
gctgcggcga gcggtatcag ctcactcaaa ggcggtaata cggttatcca cagaatcagg   3120
ggataacgca ggaaagaaca tgtgagcaaa aggccagcaa aaggccagga accgtaaaaa   3180
ggccgcgttg ctggcgtttt tccataggct ccgcccccct gacgagcatc acaaaaatcg   3240
```

-continued

```
acgctcaagt cagaggtggc gaaacccgac aggactataa agataccagg cgtttccccc      3300
tggaagctcc ctcgtgcgct ctcctgttcc gaccctgccg cttaccggat acctgtccgc      3360
cttttctccct tcgggaagcg tggcgctttc tcatagctca cgctgtaggt atctcagttc    3420
ggtgtaggtc gttcgctcca agctgggctg tgtgcacgaa ccccccgttc agcccgaccg      3480
ctgcgcctta tccggtaact atcgtcttga gtccaacccg gtaagacacg acttatcgcc     3540
actggcagca gccactggta acaggattag cagagcgagg tatgtaggcg gtgctacaga     3600
gttcttgaag tggtggccta actacggcta cactagaaga acagtatttg gtatctgcgc    3660
tctgctgaag ccagttacct tcggaaaaag agttggtagc tcttgatccg gcaaacaaac    3720
caccgctggt agcggtggtt ttttttgtttg caagcagcag attacgcgca gaaaaaaagg    3780
atctcaagaa gatcctttga tctttttctac ggggtctgac gctcagtgga acgaaaactc    3840
acgttaaggg attttggtca tgagattatc aaaaaggatc ttcacctaga tccttttaaa    3900
ttaaaaatga agttttaaat caatctaaag tatatatgag taaacttggt ctgacagtta   3960
ccaatgctta atcagtgagg cacctatctc agcgatctgt ctatttcgtt catccatagt    4020
tgcctgactc cccgtcgtgt agataactac gatacgggag ggcttaccat ctggccccag    4080
tgctgcaatg ataccgcgag acccacgctc accggctcca gatttatcag caataaacca    4140
gccagccgga agggccgagc gcagaagtgg tcctgcaact ttatccgcct ccatccagtc    4200
tattaattgt tgccgggaag ctagagtaag tagttcgcca gttaatagtt tgcgcaacgt    4260
tgttgccatt gctacaggca tcgtggtgtc acgctcgtcg tttggtatgg cttcattcag    4320
ctccggttcc caacgatcaa ggcgagttac atgatccccc atgttgtgca aaaaagcggt    4380
tagctccttc ggtcctccga tcgttgtcag aagtaagttg gccgcagtgt tatcactcat    4440
ggttatggca gcactgcata attctcttac tgtcatgcca tccgtaagat gcttttctgt    4500
gactggtgag tactcaacca agtcattctg agaatagtgt atgcggcgac cgagttgctc    4560
ttgcccggcg tcaatacggg ataataccgc gccacatagc agaactttaa aagtgctcat    4620
cattggaaaa cgttcttcgg ggcgaaaact ctcaaggatc ttaccgctgt tgagatccag    4680
ttcgatgtaa cccactcgtg cacccaactg atcttcagca tcttttactt tcaccagcgt    4740
ttctgggtga gcaaaaacag gaaggcaaaa tgccgcaaaa aagggaataa gggcgacacg    4800
gaaatgttga atactcatac tcttcctttt tcaatattat tgaagcattt atcagggtta    4860
ttgtctcatg agcggataca tatttgaatg tatttagaaa aataaacaaa tagggggttcc    4920
gcgcacattt ccccgaaaag tgccacctga cgtctaagaa accattatta tcatgacatt    4980
aacctataaa aataggcgta tcacgaggcc ctttcgtctc gcgcgtttcg gtgatgacgg    5040
tgaaaacctc tgacacatgc agctcccgga gacggtcaca gcttgtctgt aagcggatgc    5100
cgggagcaga caagcccgtc agggcgcgtc agcgggtgtt ggcgggtgtc ggggctggct    5160
taactatgcg gcatcagagc agattgtact gagagtgcac catatgcggt gtgaaatacc    5220
gcacagatgc gtaaggagaa aataccgcat caggcgccat tcgccattca ggctgcgcaa    5280
ctgttgggaa gggcgatcgg tgcgggcctc ttcgctatta cgccagctgg cgaaaggggg    5340
atgtgctgca aggcgattaa gttgggtaac gccagggttt cccagtcac gacgttgtaa     5400
aacgacggcc agt                                                        5413
```

<210> SEQ ID NO 9
<211> LENGTH: 5793
<212> TYPE: DNA
<213> ORGANISM: Artificial Sequence
<220> FEATURE:
<223> OTHER INFORMATION: pIRII-CAR.CD19_optimized

<400> SEQUENCE: 9

| | | |
|---|---|---|
| tcgagctcaa gcttcgaatt caccatgctt ctcctggtga caagccttct gctctgtgag | 60 |
| ttaccacacc cagcattcct cctgatccca gacatccaga tgacacagac tacatcctcc | 120 |
| ctgtctgcct ctctgggaga cagagtcacc atcagttgca gggcaagtca ggacattagt | 180 |
| aaatatttaa attggtatca gcaaaaacca gatggaactg ttaaactcct gatctaccat | 240 |
| acatcaagat tacactcagg agtcccatca aggttcagtg gcagtgggtc tggaacagat | 300 |
| tattctctca ccattagcaa cctggagcaa gaagatattg ccacttactt ttgccaacag | 360 |
| ggtaatacgc ttccgtacac gttcggaggg gggactaagt tggaaataaa aggctccacc | 420 |
| tctggatccg gcaagcccgg atctggcgag ggatccacca agggcgaggt gaaactgcag | 480 |
| gagtcaggac ctggcctggt ggcgccctca cagagcctgt ccgtcacatg cactgtctca | 540 |
| ggggtctcat tacccgacta tggtgtaagc tggattcgcc agcctccacg aaagggtctg | 600 |
| gagtggctgg gagtaatatg gggtagtgaa accacatact ataattcagc tctcaaatcc | 660 |
| agactgacca tcatcaagga caactccaag agccaagttt tcttaaaaat gaacagtctg | 720 |
| caaactgatg acacagccat ttactactgt gccaaacatt attactacgg tggtagctat | 780 |
| gctatggact actggggcca agggaccctca gtcaccgtct cctcagcggc cgcaattgaa | 840 |
| gttatgtatc ctcctcctta cctagacaat gagaagagca tggaaccat tatccatgtg | 900 |
| aaagggaaac accttttgtcc aagtccccta tttcccggac cttctaagcc cttttgggtg | 960 |
| ctggtggtgg ttggtggagt cctggcttgc tatagcttgc tagtaacagt ggcctttatt | 1020 |
| attttctggg tgaggagtaa gaggagcagg ctcctgcaca gtgactacat gaacatgact | 1080 |
| ccccgccgcc ccgggcccac ccgcaagcat taccagcct atgccccacc acgcgacttc | 1140 |
| gcagcctatc gctccagagt gaagttcagc aggagcgcag acgcccccgc gtaccagcag | 1200 |
| ggccagaacc agctctataa cgagctcaat ctaggacgaa gagaggagta cgatgttttg | 1260 |
| gacaagagac gtggccggga ccctgagatg gggggaaagc cgagaaggaa gaaccctcag | 1320 |
| gaaggcctgt acaatgaact gcagaaagat aagatggcgg aggcctacag tgagattggg | 1380 |
| atgaaaggcg agcgccggag gggcaagggg cacgatggcc tttaccaggg tctcagtaca | 1440 |
| gccaccaagg acacctacga cgcccttcac atgcaggccc tgcccctcg ctaaggtacc | 1500 |
| ggttgttaac gttagccggc tacgtatact ccggaatatt aataggccta ggatgcatat | 1560 |
| ggcggccgct tcccttttagt gagggttaat gcttcgagca gacatgataa gatacattga | 1620 |
| tgagtttgga caaaccacaa ctagaatgca gtgaaaaaaa tgctttattt gtgaaatttg | 1680 |
| tgatgctatt gctttatttg taaccattat aagctgcaat aaacaagtta acaacaacaa | 1740 |
| ttgcattcat tttatgtttc aggttcaggg ggagatgtgg gaggttttt aaagcaagta | 1800 |
| aaacctctac aaatgtggta aaatccgata aggatcgatc cgggctggcg taatagcgaa | 1860 |
| gaggcccgca ccgatcgccc ttcccaacag ttgcgcagcc tgaatggcga atggacgcgc | 1920 |
| cctgtagcgg cgcattaagc gcggcgggtg tggtggttac gcgcagcgtg accgctacac | 1980 |
| ttgccagcgc cctagcgccc gctcctttcg ctttcttccc ttcctttctc gccacgttcg | 2040 |
| ccggatagcg ataaggatcc gcgtatggtg cactctcagt acaatctgct ctgatgccgc | 2100 |
| atagttaagc cagccccgac acccgccaac cccgctgac gcgccctgac gggcttgtct | 2160 |
| gctcccggca tccgcttaca gacaagctgt gaccgtctcc gggatttttgt tactttatag | 2220 |

-continued

```
aagaaatttt gagttttgt ttttttttaa taaataaata aacataaata aattgtttgt      2280
tgaatttatt attagtatgt aagtgtaaat ataataaaac ttaatatcta ttcaaattaa      2340
taaataaacc tcgatataca gaccgataaa acacatgcgt caattttacg catgattatc      2400
tttaacgtac gtcacaatat gattatcttt ctagggttaa tccgggagct gcatgtgtca      2460
gaggttttca ccgtcatcac cgaaacgcgc gagacgaaag ggcctcgtga tacgcctatt      2520
tttataggtt aatgtcatga taataatggt ttcttagacg tcaggtggca cttttcgggg      2580
aaatgtgcgc ggaacccta tttgtttatt tttctaaata cattcaaata tgtatccgct      2640
catgagacaa taaccctgat aaatgcttca ataatattga aaaggaaga gtatgagtat      2700 tcaacatttc cgtgtcgccc ttattccctt ttttgcggca ttttgccttc ctgttttgc      2760 tcacccagaa acgctggtga agtaaaaga tgctgaagat cagttgggtg cacgagtggg      2820
ttacatcgaa ctggatctca acagcggtaa gatccttgag agttttcgcc ccgaagaacg      2880
ttttccaatg atgagcactt ttaaagttct gctatgtggc gcggtattat cccgtattga      2940
cgccgggcaa gagcaactcg gtcgccgcat acactattct cagaatgact tggttgagta      3000
ctcaccagtc acagaaaagc atcttacgga tggcatgaca gtaagagaat tatgcagtgc      3060
tgccataacc atgagtgata acactgcggc caacttactt ctgacaacga tcggaggacc      3120
gaaggagcta accgcttttt tgcacaacat gggggatcat gtaactcgcc ttgatcgttg      3180
ggaaccggag ctgaatgaag ccataccaaa cgacgagcgt gacaccacga tgcctgtagc      3240
aatggcaaca acgttgcgca aactattaac tggcgaacta cttactctag cttcccggca      3300
acaattaata gactggatgg aggcggataa agttgcagga ccacttctgc gctcggccct      3360
tccggctggc tggtttattg ctgataaatc tggagccggt gagcgtgggt ctcgcggtat      3420
cattgcagca ctggggccag atggtaagcc ctcccgtatc gtagttatct acacgacggg      3480
gagtcaggca actatggatg aacgaaatag acagatcgct gagataggtg cctcactgat      3540
taagcattgg taactgtcag accaagttta ctcatatata ctttagattg atttaaaact      3600
tcatttttaa tttaaaagga tctaggtgaa gatcctttt gataatctca tgaccaaaat      3660
cccttaacgt gagttttcgt tccactgagc gtcagacccc gtagaaaaga tcaaaggatc      3720
ttcttgagat ccttttttc tgcgcgtaat ctgctgcttg caaacaaaaa aaccaccgct      3780
accagcggtg gtttgtttgc cggatcaaga gctaccaact cttttccga aggtaactgg      3840 cttcagcaga gcgcagatac caaatactgt tcttctagtg tagccgtagt taggccacca      3900
cttcaagaac tctgtagcac cgcctacata cctcgctctg ctaatcctgt taccagtggc      3960
tgctgccagt ggcgataagt cgtgtcttac cgggttggac tcaagacgat agttaccgga      4020
taaggcgcag cggtcgggct gaacggggg ttcgtgcaca gcccagct tggagcgaac      4080 gacctacacc gaactgagat acctacagcg tgagctatga gaaagcgcca cgcttcccga      4140
agggagaaag gcggacaggt atccggtaag cggcagggtc ggaacaggag agcgcacgag      4200
ggagcttcca gggggaaacg cctggtatct ttatagtcct gtcgggtttc gccacctctg      4260
acttgagcgt cgatttttgt gatgctcgtc agggggggcgg agcctatgga aaaacgccag      4320
caacgcggcc ttttacggt tcctggcctt ttgctggcct tttgctcaca tggctcgaca      4380
gatctttaac cctagaaaga tagtctgcgt aaaattgacg catgcattct tgaaatattg      4440
ctctctcttt ctaaatagcg cgaatccgtc gctgtgcatt taggacatct cagtcgccgc      4500
ttggagctcc cgtgaggcgt gcttgtcaat gcggtaagtg tcactgattt tgaactataa      4560
cgaccgcgtg agtcaaaatg acgcatgatt atcttttacg tgacttttaa gatttaactc      4620
```

```
atacgataat tatattgtta tttcatgttc tacttacgtg ataacttatt atatatatat    4680
tttcttgtta tagataagat cttcaatatt ggccattagc catattattc attggttata    4740
tagcataaat caatattggc tattggccat tgcatacgtt gtatctatat cataatatgt    4800
acatttatat tggctcatgt ccaatatgac cgccatgttg gcattgatta ttgactagtt    4860
attaatagta atcaattacg gggtcattag ttcatagccc atatatggag ttccgcgtta    4920
cataacttac ggtaaatggc ccgcctggct gaccgcccaa cgaccccgc ccattgacgt     4980 caataatgac gtatgttccc atagtaacgc caatagggac tttccattga cgtcaatggg    5040
tggagtattt acggtaaact gcccacttgg cagtacatca agtgtatcat atgccaagtc    5100
cgccccctat tgacgtcaat gacggtaaat ggcccgcctg gcattatgcc cagtacatga    5160
ccttacggga ctttcctact tggcagtaca tctacgtatt agtcatcgct attaccatgg    5220
tgatgcggtt ttggcagtac accaatgggc gtggatagcg gtttgactca cggggatttc    5280
caagtctcca ccccattgac gtcaatggga gtttgttttg gcaccaaaat caacgggact    5340
ttccaaaatg tcgtaacaac tgcgatcgcc cgccccgttg acgcaaatgg gcggtaggcg    5400
tgtacggtgg gaggtctata taagcagagc tcgtttagtg aaccgtcaga tcactagaag    5460
ctttattgcg gtagtttatc acagttaaat tgctaacgca gtcagtgctt ctgacacaac    5520
agtctcgaac ttaagctgca gtgactctct taaggtagcc ttgcagaagt tggtcgtgag    5580
gcactgggca ggtaagtatc aaggttacaa gacaggttta aggagaccaa tagaaactgg    5640
gcttgtcgag acagagaaga ctcttgcgtt tctgataggc acctattggt cttactgaca    5700
tccactttgc ctttctctcc acaggtgtcc actcccagtt caattacagc tcttaaggct    5760
agagtactta atacgactca ctataggcta gcc                                 5793
```